US005627264A

United States Patent [19]

Fodor et al.

[11] Patent Number: 5,627,264
[45] Date of Patent: May 6, 1997

[54] CHIMERIC COMPLEMENT INHIBITOR PROTEINS

[75] Inventors: William L. Fodor, New Haven; Scott Rollins, Monroe; Stephen P. Squinto, Bethany, all of Conn.

[73] Assignee: Alexion Pharmaceuticals, Inc., New Haven, Conn.

[21] Appl. No.: 205,508

[22] Filed: Mar. 3, 1994

[51] Int. Cl.$^6$ .............................. C07K 19/00; C07K 14/47
[52] U.S. Cl. ........................................ 530/350; 530/380
[58] Field of Search ........................ 530/350, 380, 530/829, 830

[56] References Cited

U.S. PATENT DOCUMENTS 5,242,810  9/1993  Maraganore et al. ................. 435/69.2
5,338,669  8/1994  Gilles et al. ........................... 435/69.1

OTHER PUBLICATIONS

Adams, et al., 1991. "Contribution of the Repeating Domains of Membrane Cofactor Protein (CD46) of the Complement System to Ligand Binding and Cofactor Activity" *Journal of Immunology* 147:3005–3011.

Albrecht, et al., 1992. "Herpesvirus Saimiri Has a Gene Specifying a Homologue of the Cellular Membrane Glycoprotein CD59" *Virology* 190:527–530.

Coyne et al., 1992. "Mapping of epitopes, glycosylation sites, and complement regulatory domains in human decay accelerating factor," *Journal of Immunology* 149:2906–2913.

Davies, et al., 1989. "CD59, an LY–6–like protein expressed in human lymphoid cells, regulates the action of the complement membrane attack complex on homologous cells" *J. Exp. Med.* 170:637–654.

Lublin, et al., "Molecular cloning and chromosomal localization of human membrane cofactor protein (MCP)." *J. Exp. Med.*, 168:181–194, 1988.

Lublin, et al., "Decay–accelerating factor: Biochemistry, molecular biology, and function," *Ann. Rev. Immunol.*, 7:35–38, 1989.

Lublin, et al., "Phospholipid–anchored and Transmembrane Versions of Either Decay–accelerating Factor or Membrane Cofactor Protein Show Equal Efficiency in Protection from Complement–mediated cell Damage," *J. Exp. Med.*, 174:35–44, 1991.

Rollins, et al., 1991. "Inhibition of homologous complement by CD59 is mediated by a species–selective recognition conferred through binding to C8 within C5b–8 or C9 within C5b–9" *J. Immunol.* 146:2345–2351.

Rother, et al., 1994. "Inhibition of Complement–Mediated Cytolysis by the Terminal Complement Inhibitor of Herpesvirus Saimiri," *J. Virol.* 68:730–737.

Sawada, et al., 1990. "Isolation and expression of the full–length cDNA encoding CD59 antigen of human lymphocytes" *DNA and Cell. Biol.* 9: 213–220.

Stefanova, et al., 1989. "Characterization of a broadly expressed human leucocyte surface antigen MEM–43 anchored in membrane through phosphatidylinositol" *Mol. Immunol.* 26:153–161.

Su, et al., 1991. "The Glycosyl Phosphatidylinositol Anchor Is Critical for Ly–6A/E–mediated T Cell Activation," *J. Cell Biol.* 112:377–384.

(List continued on next page.)

Primary Examiner—Robert A. Wax
Assistant Examiner—Kawai Lau
Attorney, Agent, or Firm—Seth A. Fidel; Maurice M. Klee

[57] ABSTRACT

Chimeric complement inhibitor proteins are provided which include a first functional domain (first amino acid sequence) having C3 inhibitory activity and a second functional domain (second amino acid sequence) having C5b-9 inhibitory activity. The first functional domain is amino terminal to the second functional domain. In this way, the chimeric protein exhibits both C3 and C5b-9 inhibitory activity. The other orientation, i.e., the orientation in which the second amino acid sequence is amino terminal to the first amino acid sequence, only produces C3 inhibitory activity. Nucleic acid molecules encoding such proteins are also provided.

5 Claims, 7 Drawing Sheets

OTHER PUBLICATIONS

Tone, et al., 1992. "Gene structure of human CD59 and demonstration that discrete mRNAs are generated by alternative polyadenylation" *J. Mol. Biol.* 227:971–976.

Venneker, et al., 1992. "CD59: a molecule involved in antigen presentation as well as downregulation of membrane attack complex" *Exp. Clin. Immunogenet.* 9:33–47.

Walsh, et al., 1991. "Transfection of human CD59 complementary DNA into rat cells confers resistance to human complement" *Eur. J. Immunol.* 21:847–850.

Whitlow, et al., 1990. "H19, a surface membrane molecule involved in T-cell activation, inhibits channel formation by human complement" *Cell. Immunol.* 126:176–184.

Meri, et al., 1990. "Human protectin (CD59), an 18,000–20,000 MW complement lysis restricting factor, inhibits C5b–8 catalysed insertion of C9 into lipid bilayers" *Immunology* 71:1–9.

Moran, et al., 1992. "Human recombinant soluble decay accelerating factor inhibits complement activation in vitro and in vivo." *J. Immunol.* 149:1736–1743.

Norris, et al., 1993. "Structure–Function Relationships of CD59," *Blood,* 82 (Suppl.):202a.

Okada, et al., 1989. "Monoclonal antibodies capable of causing hemolysis of neuraminidase–treated human erythrocytes by homologous complement" *J. Immunol.* 143:2262–2266.

Perkins et al., 1988. "A Study of the Structure of Human Complement Component Factor H by Fourier Transform Infared Spectroscopy and Secondary Structure Averaging Methods," *Biochemistry,* 27:4004–4012.

Petranka, et al., 1993. "The Structure and Function of CD59: The Importance of the Disulfide Structure and Identification of a Primary Epitope," *Molec. Immunol.* 30 (suppl. 1):44.

Philbrick, et al., 1990. "The CD59 antigen is a structural homologue of murine Ly–6 antigens but lacks interferon inducibility" *Eur. J. Immunol.* 20:87–92.

Rollins, et al., 1990. "The complement–inhibitory activity of CD59 resides in its capacity to block incorporation of C9 into membrane C5b–9" *J. Immunol.* 144:3478–3483.

Wing, et al., 1992. "Oligodendrocytes lack glycolipid anchored proteins which protect them against complement lysis. Restoration of resistance to lysis by incorporation of CD59" *Immunology* 76:140–145.

Zhao, et al., 1991. "Amplified gene expression in CD59–transfected Chinese hamster ovary cells confers protection against the membrane attack complex of human complement" *J. Biol. Chem.* 266: 13418–13422.

Dalmasso, A.P. et al. (1991) "Inhibition of complement–mediated endothelial cell cytotoxicity by decay–accelerating factor" Transplantation 52(3):530–533.

Lehto, T. et al. (1993) "Interactions of soluble CD59 with the terminal complement complexes" J. Immunol. 151(9):4941–4949.

Kalli, K.R. et al. (1991) "Mapping of the C3b–binding Site of CR1 and Construction of a $(CR1)_2$–$F(ab')_2$ Chimeric Complement Inhibitor." *J. Exp. Med.* 174:1451–1460.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2096
        ( B ) TYPE: Nucleic Acid
        ( C ) STRANDEDNESS: Double
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
(A) ORGANISM: Homo sapiens ( x ) PUBLICATION INFORMATION:
(A) AUTHORS: Lublin, Douglas M.
Atkinson, John P.
(B) TITLE: Decay-Accelerating Factor:
Biochemistry, Molecular Biology, and
Function
(C) JOURNAL: Annual Review of Immunology
(D) VOLUME: 7
(F) PAGES: 35-58
(G) DATE: 1989

( x i ) SEQUENCE DESCRIPTION: SEQ ID NO:1:

```
GCTGCGACTC GGCGGAGTCC CGGCGGCGCG TCCTTGTTCT                                          40

AACCCGGCGC GCC ATG ACC GTC GCG CGG CCG AGC GTG CCC                                   80
            Met Thr Val Ala Arg Pro Ser Val Pro
                                        -30

GCG GCG CTG CCC CTC CTC GGG GAG CTG CCC CGG CTG CTG CTG              122
Ala Ala Leu Pro Leu Leu Gly Glu Leu Pro Arg Leu Leu Leu
-25              -20                     -15

CTG GTG CTG TTG TGC CTG CCG GCC GTG TGG GGT GAC TGT GGC              164
Leu Val Leu Leu Cys Leu Pro Ala Val Trp Gly Asp Cys Gly
    -10              -5                       1

CTT CCC CCA GAT GTA CCT AAT GCC CAG CCA GCT TTG GAA GGC              206
Leu Pro Pro Asp Val Pro Asn Ala Gln Pro Ala Leu Glu Gly
    5                    10                  15

CGT ACA AGT TTT CCC GAG GAT ACT GTA ATA ACG TAC AAA TGT              248
Arg Thr Ser Phe Pro Glu Asp Thr Val Ile Thr Tyr Lys Cys
        20               25                      30

GAA GAA AGC TTT GTG AAA ATT CCT GGC GAG AAG GAC TCA GTG              290
Glu Glu Ser Phe Val Lys Ile Pro Gly Glu Lys Asp Ser Val
            35                       40                  45

ACC TGC CTT AAG GGC ATG CAA TGG TCA GAT ATT GAA GAG TTC              332
Thr Cys Leu Lys Gly Met Gln Trp Ser Asp Ile Glu Glu Phe
                50                   55

TGC AAT CGT AGC TGC GAG GTG CCA ACA AGG CTA AAT TCT GCA              374
Cys Asn Arg Ser Cys Glu Val Pro Thr Arg Leu Asn Ser Ala
60                   65                       70

TCC CTC AAA CAG CCT TAT ATC ACT CAG AAT TAT TTT CCA GTC              416
Ser Leu Lys Gln Pro Tyr Ile Thr Gln Asn Tyr Phe Pro Val
    75                   80                       85

GGT ACT GTT GTG GAA TAT GAG TGC CGT CCA GGT TAC AGA AGA              458
Gly Thr Val Val Glu Tyr Glu Cys Arg Pro Gly Tyr Arg Arg
            90                   95                      100

GAA CCT TCT CTA TCA CCA AAA CTA ACT TGC CTT CAG AAT TTA              500
Glu Pro Ser Leu Ser Pro Lys Leu Thr Cys Leu Gln Asn Leu
            105                  110                     115

AAA TGG TCC ACA GCA GTC GAA TTT TGT AAA AAG AAA TCA TGC              542
Lys Trp Ser Thr Ala Val Glu Phe Cys Lys Lys Lys Ser Cys
                120                      125

CCT AAT CCG GGA GAA ATA CGA AAT GGT CAG ATT GAT GTA CCA              584
Pro Asn Pro Gly Glu Ile Arg Asn Gly Gln Ile Asp Val Pro
130                  135                      140

GGT GGC ATA TTA TTT GGT GCA ACC ATC TCC TTC TCA TGT AAC              626
Gly Gly Ile Leu Phe Gly Ala Thr Ile Ser Phe Ser Cys Asn
    145                  150                      155
```

| | | | | | | | | | | | | | | |
|---|---|---|---|---|---|---|---|---|---|---|---|---|---|---|
| ACA | GGG | TAC | AAA | TTA | TTT | GGC | TCG | ACT | TCT | AGT | TTT | TGT | CTT | 668 |
| Thr | Gly | Tyr | Lys | Leu | Phe | Gly | Ser | Thr | Ser | Ser | Phe | Cys | Leu | |
| | | 160 | | | | 165 | | | | | 170 | | | |
| ATT | TCA | GGC | AGC | TCT | GTC | CAG | TGG | AGT | GAC | CCG | TTG | CCA | GAG | 710 |
| Ile | Ser | Gly | Ser | Ser | Val | Gln | Trp | Ser | Asp | Pro | Leu | Pro | Glu | |
| | | | 175 | | | | 180 | | | | | 185 | | |
| TGC | AGA | GAA | ATT | TAT | TGT | CCA | GCA | CCA | CAA | ATT | GAC | AAT | | 752 |
| Cys | Arg | Glu | Ile | Tyr | Cys | Pro | Ala | Pro | Gln | Ile | Asp | Asn | | |
| | | | | 190 | | | | 195 | | | | | | |
| GGA | ATA | ATT | CAA | GGG | GAA | CGT | GAC | CAT | TAT | GGA | TAT | AGA | CAG | 794 |
| Gly | Ile | Ile | Gln | Gly | Glu | Arg | Asp | His | Tyr | Gly | Tyr | Arg | Gln | |
| 200 | | | | | 205 | | | | | 210 | | | | |
| TCT | GTA | ACG | TAT | GCA | TGT | AAT | AAA | GGA | TTC | ACC | ATG | ATT | GGA | 836 |
| Ser | Val | Thr | Tyr | Ala | Cys | Asn | Lys | Gly | Phe | Thr | Met | Ile | Gly | |
| | 215 | | | | | 220 | | | | | 225 | | | |
| GAG | CAC | TCT | ATT | TAT | TGT | ACT | GTG | AAT | AAT | GAT | GAA | GGA | GAG | 878 |
| Glu | His | Ser | Ile | Tyr | Cys | Thr | Val | Asn | Asn | Asp | Glu | Gly | Glu | |
| | | 230 | | | | | 235 | | | | | 240 | | |
| TGG | AGT | GGC | CCA | CCA | CCT | GAA | TGC | AGA | GGA | AAA | TCT | CTA | ACT | 920 |
| Trp | Ser | Gly | Pro | Pro | Pro | Glu | Cys | Arg | Gly | Lys | Ser | Leu | Thr | |
| | | | 245 | | | | | 250 | | | | | 255 | |
| TCC | AAG | GTC | CCA | CCA | ACA | GTT | CAG | AAA | CCT | ACC | ACA | GTA | AAT | 962 |
| Ser | Lys | Val | Pro | Pro | Thr | Val | Gln | Lys | Pro | Thr | Thr | Val | Asn | |
| | | | | 260 | | | | | 265 | | | | | |
| GTT | CCA | ACT | ACA | GAA | GTC | TCA | CCA | ACT | TCT | CAG | AAA | ACC | ACC | 1004 |
| Val | Pro | Thr | Thr | Glu | Val | Ser | Pro | Thr | Ser | Gln | Lys | Thr | Thr | |
| 270 | | | | | 275 | | | | | 280 | | | | |
| ACA | AAA | ACC | ACC | ACA | CCA | AAT | GCT | CAA | GCA | ACA | CGG | AGT | ACA | 1046 |
| Thr | Lys | Thr | Thr | Thr | Pro | Asn | Ala | Gln | Ala | Thr | Arg | Ser | Thr | |
| | 285 | | | | | 290 | | | | | 295 | | | |
| CCT | GTT | TCC | AGG | ACA | ACC | AAG | CAT | TTT | CAT | GAA | ACA | ACC | CCA | 1088 |
| Pro | Val | Ser | Arg | Thr | Thr | Lys | His | Phe | His | Glu | Thr | Thr | Pro | |
| | | 300 | | | | | 305 | | | | | 310 | | |
| AAT | AAA | GGA | AGT | GGA | ACC | ACT | TCA | GGT | ACT | ACC | CGT | CTT | CTA | 1130 |
| Asn | Lys | Gly | Ser | Gly | Thr | Thr | Ser | Gly | Thr | Thr | Arg | Leu | Leu | |
| | | | 315 | | | | | 320 | | | | | 325 | |
| TCT | GGG | CAC | ACG | TGT | TTC | ACG | TTG | ACA | GGT | TTG | CTT | GGG | ACG | 1172 |
| Ser | Gly | His | Thr | Cys | Phe | Thr | Leu | Thr | Gly | Leu | Leu | Gly | Thr | |
| | | | | 330 | | | | | 335 | | | | | |
| CTA | GTA | ACC | ATG | GGC | TTG | CTG | ACT | | | | | | | 1196 |
| Leu | Val | Thr | Met | Gly | Leu | Leu | Thr | | | | | | | |
| 340 | | | | | 345 | | | | | | | | | |
| TAGCCAAAGA | AGAGTTAAGA | AGAAAATACA | CACAAGTATA | CAGACTGTTC | | | | | | | | | | 1246 |
| CTAGTTTCTT | AGACTTATCT | GCATATTGGA | TAAAATAAAT | GCAATTGTGC | | | | | | | | | | 1296 |
| TCTTCATTTA | GGATGCTTTC | ATTGTCTTTA | AGATGTGTTA | GGAATGTCAA | | | | | | | | | | 1346 |
| CAGAGCAAGG | AGAAAAAAGG | CAGTCCTGGA | ATCACATTCT | TAGCACACCT | | | | | | | | | | 1396 |
| GCGCCTCTTG | AAAATAGAAC | AACTTGCAGA | ATTGAGAGTG | ATTCCTTTCC | | | | | | | | | | 1446 |
| TAAAAGTGTA | AGAAAGCATA | GAGATTTGTT | CGTATTAAGA | ATGGGATCAC | | | | | | | | | | 1496 |
| GAGGAAAAGA | GAAGGAAAGT | GATTTTTTTC | CACAAGATCT | GAAATGATAT | | | | | | | | | | 1546 |
| TTCCACTTAT | AAAGGAAATA | AAAAATGAAA | AACATTATTT | GGATATCAAA | | | | | | | | | | 1596 |
| AGCAAATAAA | AACCCAATTC | AGTCTCTTCT | AAGCAAAATT | GCTAAAGAGA | | | | | | | | | | 1646 |
| GATGACCACA | TTATAAAGTA | ATCTTTGGCT | AAGGCATTTT | CATCTTTCCT | | | | | | | | | | 1696 |
| TCGGTTGGCA | AAATATTTTA | AAGGTAAAAC | ATGCTGGTGA | ACCAGGGTGT | | | | | | | | | | 1746 |
| TGATGGTGAT | AAGGGAGGAA | TATAGAATGA | AAGACTGAAT | CTTCCTTTGT | | | | | | | | | | 1796 |

```
TGCACAAATA  GAGTTTGGAA  AAAGCCTGTG  AAAGGTGTCT  TCTTTGACTT                1846

AATGTCTTTA  AAAGTATCCA  GAGATACTAC  AATATTAACA  TAAGAAAAGA                1896

TTATATATTA  TTTCTGAATC  GAGATGTCCA  TAGTCAAATT  TGTAAATCTT                1946

ATTCTTTTGT  AATATTTATT  TATATTTATT  TATGACAGTG  AACATTCTGA                1996

TTTTACATGT  AAAACAAGAA  AAGTTGAAGA  AGATATGTGA  AGAAAAATGT                2046

ATTTTTCCTA  AATAGAAATA  AATGATCCCA  TTTTTGGTA   AAAAAAAAA                 2096
```

(2) INFORMATION FOR SEQ ID NO:2:

(i) SEQUENCE CHARACTERISTICS:
        (A) LENGTH: 1139 bases
        (B) TYPE: Nucleic Acid
        (C) STRANDEDNESS: Double
        (D) TOPOLOGY: Linear (ii) MOLECULE TYPE: cDNA to mRNA
        (A) DESCRIPTION: CD59 full length cDNA (iii) HYPOTHETICAL: No (iv) ANTI-SENSE: No (vi) ORIGINAL SOURCE:
        (A) ORGANISM: Homo sapiens (x) PUBLICATION INFORMATION:
        (A) AUTHORS: Philbrick, W.M.
                Palfree, R.G.E
                Maher, S.E.
                Bridgett, M.M.
                Sirlin S.
                Bothwell, A.L.M.
        (B) TITLE: The CD59 antigen is a structural
            homologue of murine Ly-6 antigens but
            lacks interferon inducibility.
        (C) JOURNAL: European Journal of Immunology
        (D) VOLUME: 20
        (F) PAGES: 87-92
        (G) DATE: JAN-1990

(xi) SEQUENCE DESCRIPTION: SEQ ID NO:2:

```
CGCAGAAGCG  GCTCGAGGCT  GGAAGAGGAT  CCTGGGCGCC  GCAGGTTCTG                 50

TGGACAATCA  CA  ATG GGA ATC CAA GGA GGG TCT GTC CTG TTC                   92
                Met Gly Ile Gln Gly Gly Ser Val Leu Phe
                -25                     -20

GGG CTG CTG CTC GTC CTG GCT GTC TTC TGC CAT TCA GGT CAT                   134
Gly Leu Leu Leu Val Leu Ala Val Phe Cys His Ser Gly His
-15              -10                      -5

AGC CTG CAG TGC TAC AAC TGT CCT AAC CCA ACT GCT GAC TGC                   176
Ser Leu Gln Cys Tyr Asn Cys Pro Asn Pro Thr Ala Asp Cys
    +1              5                    10

AAA ACA GCC GTC AAT TGT TCA TCT GAT TTT GAT GCG TGT CTC                   218
Lys Thr Ala Val Asn Cys Ser Ser Asp Phe Asp Ala Cys Leu
    15              20                   25

ATT ACC AAA GCT GGG TTA CAA GTG TAT AAC AAG TGT TGG AAG                   260
Ile Thr Lys Ala Gly Leu Gln Val Tyr Asn Lys Cys Trp Lys
        30              35                   40

TTT GAG CAT TGC AAT TTC AAC GAC GTC ACA ACC CGC TTG AGG                   302
Phe Glu His Cys Asn Phe Asn Asp Val Thr Thr Arg Leu Arg
            45              50                   55

GAA AAT GAG CTA ACG TAC TAC TGC TGC AAG AAG GAC CTG TGT                   344
Glu Asn Glu Leu Thr Tyr Tyr Cys Cys Lys Lys Asp Leu Cys
                60              65

AAC TTT AAC GAA CAG CTT GAA AAT GGT GGG ACA TCC TTA TCA                   386
```

| Asn | Phe | Asn | Glu | Gln | Leu | Glu | Asn | Gly | Gly | Thr | Ser | Leu | Ser | | |
|---|---|---|---|---|---|---|---|---|---|---|---|---|---|---|---|
| 70 | | | | | 75 | | | | | 80 | | | | | |

| GAG | AAA | ACA | GTT | CTT | CTG | CTG | GTG | ACT | CCA | TTT | CTG | GCA | GCA | | 428 |
|---|---|---|---|---|---|---|---|---|---|---|---|---|---|---|---|
| Glu | Lys | Thr | Val | Leu | Leu | Leu | Val | Thr | Pro | Phe | Leu | Ala | Ala | | |
| | 85 | | | | | 90 | | | | | 95 | | | | |

| GCC | TGG | AGC | CTT | CAT | CCC | TAA | G TCAACACCAG GAGAGCTTCT | | 470 |
|---|---|---|---|---|---|---|---|---|---|
| Ala | Trp | Ser | Leu | His | Pro | | | | |
| | | 100 | | | | | | | |

```
CCCAAACTCC  CCGTTCCTGC  GTAGTCCGCT  TTCTCTTGCT  GCCACATTCT                520
AAAGGCTTGA  TATTTTCCAA  ATGGATCCTG  TTGGGAAAGA  ATAAAATTAG                570
CTTGAGCAAC  CTGGCTAAGA  TAGAGGGGTC  TGGGAGACTT  TGAAGACCAG                620
TCCTGCCCGC  AGGGAAGCCC  CACTTGAAGG  AAGAAGTCTA  AGAGTGAAGT                670
AGGTGTGACT  TGAACTAGAT  TGCATGCTTC  CTCCTTTGCT  CTTGGGAAGA                720
CCAGCTTTGC  AGTGACAGCT  TGAGTGGGTT  CTCTGCAGCC  CTCAGATTAT                770
TTTTCCTCTG  GCTCCTTGGA  TGTAGTCAGT  TAGCATCATT  AGTACATCTT                820
TGGAGGGTGG  GGCAGGAGTA  TATGAGCATC  CTCTCTCACA  TGGAACGCTT                870
TCATAAACTT  CAGGGATCCC  GTGTTGCCAT  GGAGGCATGC  CAAATGTTCC                920
ATATGTGGGT  GTCAGTCAGG  GACAACAAGA  TCCTTAATGC  AGAGCTAGAG                970
GACTTCTGGC  AGGGAAGTGG  GGAAGTGTTC  CAGATTCCAG  ATAGCAGGGC               1020
ATGAAAACTT  AGAGAGGTAC  AAGTGGCTGA  AAATCGAGTT  TTTCCTCTGT               1070
CTTTAAATTT  TATATGGGCT  TTGTTATCTT  CCACTGGAAA  AGTGTAATAG               1120
CATACATCAA  TGGTGTGTT                                                    1139
```

( 2 ) INFORMATION FOR SEQ ID NO:3:

( i ) SEQUENCE CHARACTERISTICS:
        ( A ) LENGTH: 1530 bases
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: MCP (CD46) full length cDNA ( i i i ) HYPOTHETICAL: No ( i v ) ANTI-SENSE: No ( v i ) ORIGINAL SOURCE:
        ( A ) ORGANISM: Homo sapiens ( x ) PUBLICATION INFORMATION:
        ( A ) AUTHORS: Lublin, D.M.
                Liszewski,M.K.
                Post, T.W.
                Arce, M.A.
                LeBeau, M.M.
                Rebentisch, M.B.
                Lemons, R.S.
                Seya, T.
                Atkinson, J.P.
        ( B ) TITLE: Molecular cloning and Chromosomal
                Localization of Membrane Cofactor
                Protein (MCP): Evidence for Inclusion
                in the Multi-Gene Family of
                Complement- Regulatory Proteins.
        ( C ) JOURNAL: Journal of Experimental Medicine
        ( D ) VOLUME: 168
        ( F ) PAGES: 181-194
        ( G ) DATE: 1988

( x i ) SEQUENCE DESCRIPTION: SEQ ID NO:3:

-continued

| | | | | | | | | | | | | | |
|---|---|---|---|---|---|---|---|---|---|---|---|---|---|
| TCTGCTTTCC | TCCGGAGAAA | TAACAGCGTC | TTCCGCGCCG | CGC | ATG | GAG | | | | | | | 49 |
| | | | | | Met | Glu | | | | | | | |
| | | | | | -34 | | | | | | | | |

| CCT | CCC | GGC | CGC | CGC | GAG | TGT | CCC | TTT | CCT | TCC | TGG | CGC | TTT | 91 |
|---|---|---|---|---|---|---|---|---|---|---|---|---|---|---|
| Pro | Pro | Gly | Arg | Arg | Glu | Cys | Pro | Phe | Pro | Ser | Trp | Arg | Phe | |
| | | -30 | | | | -25 | | | | | | -20 | | |

| CCT | GGG | TTG | CTT | CTG | GCG | GCC | ATG | GTG | TTG | CTG | CTG | TAC | TCC | 133 |
|---|---|---|---|---|---|---|---|---|---|---|---|---|---|---|
| Pro | Gly | Leu | Leu | Leu | Ala | Ala | Met | Val | Leu | Leu | Leu | Tyr | Ser | |
| | | | -15 | | | | | -10 | | | | | -5 | |

| TTC | TCC | GAT | GCC | TGT | GAG | GAG | CCA | CCA | ACA | TTT | GAA | GCT | ATG | 175 |
|---|---|---|---|---|---|---|---|---|---|---|---|---|---|---|
| Phe | Ser | Asp | Ala | Cys | Glu | Glu | Pro | Pro | Thr | Phe | Glu | Ala | Met | |
| | | | | 1 | | | | 5 | | | | | 10 | |

| GAG | CTC | ATT | GGT | AAA | CCA | AAA | CCC | TAC | TAT | GAG | ATT | GGT | GAA | 217 |
|---|---|---|---|---|---|---|---|---|---|---|---|---|---|---|
| Glu | Leu | Ile | Gly | Lys | Pro | Lys | Pro | Tyr | Tyr | Glu | Ile | Gly | Glu | |
| | | | | 15 | | | | | 20 | | | | | |

| CGA | GTA | GAT | TAT | AAG | TGT | AAA | AAA | GGA | TAC | TTC | TAT | ATA | CCT | 259 |
|---|---|---|---|---|---|---|---|---|---|---|---|---|---|---|
| Arg | Val | Asp | Tyr | Lys | Cys | Lys | Lys | Gly | Tyr | Phe | Tyr | Ile | Pro | |
| 25 | | | | | 30 | | | | | 35 | | | | |

| CCT | CTT | GCC | ACC | CAT | ACT | ATT | TGT | GAT | CGG | AAT | CAT | ACA | TGG | 301 |
|---|---|---|---|---|---|---|---|---|---|---|---|---|---|---|
| Pro | Leu | Ala | Thr | His | Thr | Ile | Cys | Asp | Arg | Asn | His | Thr | Trp | |
| | | 40 | | | | | 45 | | | | | 50 | | |

| CTA | CCT | GTC | TCA | GAT | GAC | GCC | TGT | TAT | AGA | GAA | ACA | TGT | CCA | 343 |
|---|---|---|---|---|---|---|---|---|---|---|---|---|---|---|
| Leu | Pro | Val | Ser | Asp | Asp | Ala | Cys | Tyr | Arg | Glu | Thr | Cys | Pro | |
| | | 55 | | | | | 60 | | | | | 65 | | |

| TAT | ATA | CGG | GAT | CCT | TTA | AAT | GGC | CAA | GCA | GTC | CCT | GCA | AAT | 385 |
|---|---|---|---|---|---|---|---|---|---|---|---|---|---|---|
| Tyr | Ile | Arg | Asp | Pro | Leu | Asn | Gly | Gln | Ala | Val | Pro | Ala | Asn | |
| | | | 70 | | | | | 75 | | | | | 80 | |

| GGG | ACT | TAC | GAG | TTT | GGT | TAT | CAG | ATG | CAC | TTT | ATT | TGT | AAT | 427 |
|---|---|---|---|---|---|---|---|---|---|---|---|---|---|---|
| Gly | Thr | Tyr | Glu | Phe | Gly | Tyr | Gln | Met | His | Phe | Ile | Cys | Asn | |
| | | | | 85 | | | | | 90 | | | | | |

| GAG | GGT | TAT | TAC | TTA | ATT | GGT | GAA | GAA | ATT | CTA | TAT | TGT | GAA | 469 |
|---|---|---|---|---|---|---|---|---|---|---|---|---|---|---|
| Glu | Gly | Tyr | Tyr | Leu | Ile | Gly | Glu | Glu | Ile | Leu | Tyr | Cys | Glu | |
| 95 | | | | | 100 | | | | | 105 | | | | |

| CTT | AAA | GGA | TCA | GTA | GCA | ATT | TGG | AGC | GGT | AAG | CCC | CCA | ATA | 511 |
|---|---|---|---|---|---|---|---|---|---|---|---|---|---|---|
| Leu | Lys | Gly | Ser | Val | Ala | Ile | Trp | Ser | Gly | Lys | Pro | Pro | Ile | |
| | 110 | | | | | 115 | | | | | 120 | | | |

| TGT | GAA | AAG | GTT | TTG | TGT | ACA | CCA | CCT | CCA | AAA | ATA | AAA | AAT | 553 |
|---|---|---|---|---|---|---|---|---|---|---|---|---|---|---|
| Cys | Glu | Lys | Val | Leu | Cys | Thr | Pro | Pro | Pro | Lys | Ile | Lys | Asn | |
| | | 125 | | | | | 130 | | | | | 135 | | |

| GGA | AAA | CAC | ACC | TTT | AGT | GAA | GTA | GAA | GTA | TTT | GAG | TAT | CTT | 595 |
|---|---|---|---|---|---|---|---|---|---|---|---|---|---|---|
| Gly | Lys | His | Thr | Phe | Ser | Glu | Val | Glu | Val | Phe | Glu | Tyr | Leu | |
| | | | 140 | | | | | 145 | | | | | 150 | |

| GAT | GCA | GTA | ACT | TAT | AGT | TGT | GAT | CCT | GCA | CCT | GGA | CCA | GAT | 637 |
|---|---|---|---|---|---|---|---|---|---|---|---|---|---|---|
| Asp | Ala | Val | Thr | Tyr | Ser | Cys | Asp | Pro | Ala | Pro | Gly | Pro | Asp | |
| | | | | 155 | | | | | 160 | | | | | |

| CCA | TTT | TCA | CTT | ATT | GGA | GAG | AGC | ACG | ATT | TAT | TGT | GGT | GAC | 679 |
|---|---|---|---|---|---|---|---|---|---|---|---|---|---|---|
| Pro | Phe | Ser | Leu | Ile | Gly | Glu | Ser | Thr | Ile | Tyr | Cys | Gly | Asp | |
| 165 | | | | | 170 | | | | | 175 | | | | |

| AAT | TCA | GTG | TGG | AGT | CGT | GCT | GCT | CCA | GAG | TGT | AAA | GTG | GTC | 721 |
|---|---|---|---|---|---|---|---|---|---|---|---|---|---|---|
| Asn | Ser | Val | Trp | Ser | Arg | Ala | Ala | Pro | Glu | Cys | Lys | Val | Val | |
| | 180 | | | | | 185 | | | | | 190 | | | |

| AAA | TGT | CGA | TTT | CCA | GTA | GTC | GAA | AAT | GGA | AAA | CAG | ATA | TCA | 763 |
|---|---|---|---|---|---|---|---|---|---|---|---|---|---|---|
| Lys | Cys | Arg | Phe | Pro | Val | Val | Glu | Asn | Gly | Lys | Gln | Ile | Ser | |
| | | 195 | | | | | 200 | | | | | 205 | | |

| GGA | TTT | GGA | AAA | AAA | TTT | TAC | TAC | AAA | GCA | ACA | GTT | ATG | TTT | 805 |
|---|---|---|---|---|---|---|---|---|---|---|---|---|---|---|
| Gly | Phe | Gly | Lys | Lys | Phe | Tyr | Tyr | Lys | Ala | Thr | Val | Met | Phe | |
| | | | 210 | | | | | 215 | | | | | 220 | |

| GAA | TGC | GAT | AAG | GGT | TTT | TAC | CTC | GAT | GGC | AGC | GAC | ACA | ATT | 847 |
|---|---|---|---|---|---|---|---|---|---|---|---|---|---|---|
| Glu | Cys | Asp | Lys | Gly | Phe | Tyr | Leu | Asp | Gly | Ser | Asp | Thr | Ile | |
| | | | | 225 | | | | | 230 | | | | | |

| | | | | | | | | | | | | | |
|---|---|---|---|---|---|---|---|---|---|---|---|---|---|
| GTC | TGT | GAC | AGT | AAC | AGT | ACT | TGG | GAT | CCC | CCA | GTT | CCA | AAG | 889 |
| Val | Cys | Asp | Ser | Asn | Ser | Thr | Trp | Asp | Pro | Pro | Val | Pro | Lys | |
| 235 | | | | 240 | | | | | 245 | | | | | |
| TGT | CTT | AAA | GTG | TCG | ACT | TCT | TCC | ACT | ACA | AAA | TCT | CCA | GCG | 931 |
| Cys | Leu | Lys | Val | Ser | Thr | Ser | Ser | Thr | Thr | Lys | Ser | Pro | Ala | |
| | 250 | | | | | 255 | | | | | 260 | | | |
| TCC | AGT | GCC | TCA | GGT | CCT | AGG | CCT | ACT | TAC | AAG | CCT | CCA | GTC | 973 |
| Ser | Ser | Ala | Ser | Gly | Pro | Arg | Pro | Thr | Tyr | Lys | Pro | Pro | Val | |
| | | 265 | | | | 270 | | | | | 275 | | | |
| TCA | AAT | TAT | CCA | GGA | TAT | CCT | AAA | CCT | GAG | GAA | GGA | ATA | CTT | 1015 |
| Ser | Asn | Tyr | Pro | Gly | Tyr | Pro | Lys | Pro | Glu | Glu | Gly | Ile | Leu | |
| | | | 280 | | | | 285 | | | | | 290 | | |
| GAC | AGT | TTG | GAT | GTT | TGG | GTC | ATT | GCT | GTG | ATT | GTT | ATT | GCC | 1057 |
| Asp | Ser | Leu | Asp | Val | Trp | Val | Ile | Ala | Val | Ile | Val | Ile | Ala | |
| | | | | 295 | | | | 300 | | | | | | |
| ATA | GTT | GTT | GGA | GTT | GCA | GTA | ATT | TGT | GTT | GTC | CCG | TAC | AGA | 1099 |
| Ile | Val | Val | Gly | Val | Ala | Val | Ile | Cys | Val | Val | Pro | Tyr | Arg | |
| 305 | | | | 310 | | | | | 315 | | | | | |
| TAT | CTT | CAA | AGG | AGG | AAG | AAG | AAA | GGG | AAA | GCA | GAT | GGT | GGA | 1141 |
| Tyr | Leu | Gln | Arg | Arg | Lys | Lys | Lys | Gly | Lys | Ala | Asp | Gly | Gly | |
| | 320 | | | | | 325 | | | | | 330 | | | |
| GCT | GAA | TAT | GCC | ACT | TAC | CAG | ACT | AAA | TCA | ACC | ACT | CCA | GCA | 1183 |
| Ala | Glu | Tyr | Ala | Thr | Tyr | Gln | Thr | Lys | Ser | Thr | Thr | Pro | Ala | |
| | | 335 | | | | 340 | | | | | 345 | | | |

| | | | | | |
|---|---|---|---|---|---|
| GAG | CAG | AGA | GGC | TGA AT AGATTCCACA ACCTGGTTTG CCAGTTCATC | 1230 |
| Glu | Gln | Arg | Gly | | |
| | | | 350 | | |

| | | |
|---|---|---|
| TTTTGACTCT | ATTAAAATCT TCAATAGTTG TTATTCTGTA GTTTCACTCT | 1280 |
| CATGAGTGCA | ACTGTGGCTT AGCTAATATT GCAATGTGGC TTGAATGTAG | 1330 |
| GTAGCATCCT | TTGATGCTTC TTTGAAACTT GTATGAATTT GGGTATGAAC | 1380 |
| AGATTGCCTG | CTTTCCCTTA ATAACACTT AGATTATTG GACCAGTCAG | 1430 |
| CACAGCATGC | CTGGTTGTAT TAAAGCAGGG ATATGCTGTA TTTTATAAAA | 1480 |
| TTGGCAAAAT | TAGAGAAATA TAGTTCACAA TGAAATTATA TTTCTTTGT | 1530 |

( 2 ) INFORMATION FOR SEQ ID NO:4:

( i ) SEQUENCE CHARACTERISTICS:
        ( A ) LENGTH: 763 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: BABCIP full length cDNA ( i i i ) HYPOTHETICAL: No ( i v ) ANTI-SENSE: No ( v i ) ORIGINAL SOURCE:
        ( A ) ORGANISM: Papio hamadryas ( v i i ) IMMEDIATE SOURCE:
        ( A ) LIBRARY: Baboon Spleen Lambda ZAPII cDNA
            Library, Catalog #936103,
            Stratagene Cloning Systems,
            La Jolla, California ( x i ) SEQUENCE DESCRIPTION: SEQ ID NO:4:

| | | |
|---|---|---|
| GGTTATGTGC | CCACACTTGC CTAGGCTGTG AATAGTTAGT ACCTCTGATT | 50 |
| ACTTAGTTAA | ATATGCTTCT AGATGAGAAG TAGCGAAAGG CTGGAAGGGA | 100 |
| TCCCGGGCGC | CGCCAGGTTC TGTGGACAAT CACA ATG GGA | 140 |
| | Met Gly | |

```
ATC CAA GGA GGG TCT GTC CTG TTC GGG CTG CTG CTT GTC CTG GCT           185
Ile Gln Gly Gly Ser Val Leu Phe Gly Leu Leu Leu Val Leu Ala
        -20              -15                     -10

GTC TTC TGC CAT TCA GGT CAT AGC CTG CAG TGC TAC AAC TGT CCT           230
Val Phe Cys His Ser Gly His Ser Leu Gln Cys Tyr Asn Cys Pro
         -5              1                   5

AAC CCA ACT ACT GAC TGC AAA ACA GCC ATC AAT TGT TCA TCT GGT           275
Asn Pro Thr Thr Asp Cys Lys Thr Ala Ile Asn Cys Ser Ser Gly
         10                  15                 20

TTT GAT ACG TGT CTC ATT GCC AGA GCT GGG TTA CAA GTA TAT AAC           320
Phe Asp Thr Cys Leu Ile Ala Arg Ala Gly Leu Gln Val Tyr Asn
         25                  30                 35

CAG TGT TGG AAG TTT GCG AAT TGC AAT TTC AAT GAC ATT TCA ACC           365
Gln Cys Trp Lys Phe Ala Asn Cys Asn Phe Asn Asp Ile Ser Thr
         40                  45                 50

CTC TTG AAG GAA AGC GAG CTA CAG TAC TTC TGC TGC AAG AAG GAC           410
Leu Leu Lys Glu Ser Glu Leu Gln Tyr Phe Cys Cys Lys Lys Asp
         55                  60                 65

CTG TGT AAC TTT AAC GAA CAG CTT GAA AAT GGT GGG ACA TCC TTA           455
Leu Cys Asn Phe Asn Glu Gln Leu Glu Asn Gly Gly Thr Ser Leu
         70                  75                 80

TCA GAG AAA ACA GTT GTT CTG CTG GTG ACC CTA CTT CTG GCA GCA           500
Ser Glu Lys Thr Val Val Leu Leu Val Thr Leu Leu Leu Ala Ala
         85                  90                 95

GCC TGG TGC CTT CAT CCC TAAGTCAACA CCAGGAGAGC TTCTCCCATA              548
Ala Trp Cys Leu His Pro
         100

CTCCCCGTTC CTGCGTAGTC CCCTTTCCCT CGTGCNGATT CTAAAGGCTT                598

ATATTTTCCA ACCGGATCCT GTTGGGAAAG AATAAAATTG ACTTGAGCAA                648

CCTGGCTAAG ATAGAGGGGC TCTGGAAGAC TTCGAAGACC AGTCCTGTTT                698

GCAGGGAAGC CCCACTTGAA GGAAGAAGTT TAAGAGTGAA GTAGGTGTGA                748

CTTGAGCTAG ATTGG                                                      763
```

( 2 ) INFORMATION FOR SEQ ID NO:5:

( i ) SEQUENCE CHARACTERISTICS:
        ( A ) LENGTH: 469 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: AGMCIP full length cDNA ( i i i ) HYPOTHETICAL: No ( i v ) ANTI-SENSE: No ( v i ) ORIGINAL SOURCE:
        ( A ) ORGANISM: Cercopithecus aethiops
        ( H ) CELL LINE: COS-1 (ATCC CRL 1650)

( x i ) SEQUENCE DESCRIPTION: SEQ ID NO:5:

```
                                TTCTGTGGAC AATCACA ATG GGA ATC         26
                                                    Met Gly Ile
                                                    -25

CAA GGA GGG TCT GTC CTG TTC GGG CTG CTG CTT GCC CTG GCT GTC            71
Gln Gly Gly Ser Val Leu Phe Gly Leu Leu Leu Ala Leu Ala Val
        -20              -15                     -10

TTC TGC CAT TCA GGT CAT AGC CTG CAA TGC TAC AAC TGT CCT AAC           116
Phe Cys His Ser Gly His Ser Leu Gln Cys Tyr Asn Cys Pro Asn
         -5              1                   5
```

-continued

```
            - 5                              1                        5
CCA  ACT  ACT  AAC  TGC  AAA  ACA  GCC  ATC  AAT  TGT  TCA  TCT  GGT  TTT        161
Pro  Thr  Thr  Asn  Cys  Lys  Thr  Ala  Ile  Asn  Cys  Ser  Ser  Gly  Phe
          10                        15                        20

GAT  ACG  TGT  CTC  ATT  GCC  AGA  GCT  GGG  TTA  CAA  GTA  TAT  AAC  CAG        206
Asp  Thr  Cys  Leu  Ile  Ala  Arg  Ala  Gly  Leu  Gln  Val  Tyr  Asn  Gln
          25                        30                        35

TGT  TGG  AAG  TTT  GCG  AAT  TGC  AAT  TTC  AAT  GAC  ATT  TCA  ACC  CTC        251
Cys  Trp  Lys  Phe  Ala  Asn  Cys  Asn  Phe  Asn  Asp  Ile  Ser  Thr  Leu
          40                        45                        50

TTG  AAG  GAA  AGC  GAG  CTA  CAG  TAC  TTC  TGC  TGC  AAG  GAG  GAC  CTG        296
Leu  Lys  Glu  Ser  Glu  Leu  Gln  Tyr  Phe  Cys  Cys  Lys  Glu  Asp  Leu
          55                        60                        65

TGT  AAC  GAA  CAG  CTT  GAA  AAT  GGT  GGG  ACA  TCC  TTA  TCA  GAG  AAA        341
Cys  Asn  Glu  Gln  Leu  Glu  Asn  Gly  Gly  Thr  Ser  Leu  Ser  Glu  Lys
          70                        75                        80

ACA  GTT  CTT  CTG  CTG  GTG  ACC  CCA  CTT  CTG  GCA  GCA  GCC  TGG  TGC        386
Thr  Val  Leu  Leu  Leu  Val  Thr  Pro  Leu  Leu  Ala  Ala  Ala  Trp  Cys
          85                        90                        95

CTT  CAT  CCC  TAAGTCAACA  CCAGGAGAGC  TTCTCCCATA  CTCCCCGTTC                    435
Leu  His  Pro
          100

CTGCGTAGTC  CCCTTTCCCC  GGCCGCATTC  TAAA                                         469
```

( 2 ) INFORMATION FOR SEQ ID NO:6:

( i ) SEQUENCE CHARACTERISTICS:
        ( A ) LENGTH: 396 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: SQMCIP full coding cDNA ( i i i ) HYPOTHETICAL: No ( i v ) ANTI-SENSE: No ( v i ) ORIGINAL SOURCE:
        ( A ) ORGANISM: Saimiri sciureus
        ( H ) CELL LINE: DPSO 114/74 (ATCC CCL 194)

( x i ) SEQUENCE DESCRIPTION: SEQ ID NO:6:

```
ATG  GGA  ATC  CAA  GGA  GGG  TCT  GTC  CTG  TTT  GGG  CTG  CTG  CTC  GTC         45
Met  Gly  Ile  Gln  Gly  Gly  Ser  Val  Leu  Phe  Gly  Leu  Leu  Leu  Val
-25                      -20                       -15

CTG  GCT  GTC  TTC  TGC  CAT  TCA  GGT  AAT  AGC  CTG  CAA  TGC  TAC  AGC         90
Leu  Ala  Val  Phe  Cys  His  Ser  Gly  Asn  Ser  Leu  Gln  Cys  Tyr  Ser
-10                      - 5                         1                    5

TGT  CCT  CTC  CCA  ACC  ATG  GAG  TCC  ATG  GAG  TGC  ACT  GCG  TCC  ACC        135
Cys  Pro  Leu  Pro  Thr  Met  Glu  Ser  Met  Glu  Cys  Thr  Ala  Ser  Thr
          10                        15                        20

AAC  TGT  ACA  TCT  AAT  CTT  GAT  TCG  TGT  CTC  ATT  GCC  AAA  GCC  GGG        180
Asn  Cys  Thr  Ser  Asn  Leu  Asp  Ser  Cys  Leu  Ile  Ala  Lys  Ala  Gly
          25                        30                        35

TCA  GGA  GTA  TAT  TAC  CGG  TGT  TGG  AAG  TTT  GAC  GAT  TGC  AGT  TTC        225
Ser  Gly  Val  Tyr  Tyr  Arg  Cys  Trp  Lys  Phe  Asp  Asp  Cys  Ser  Phe
          40                        45                        50

AAA  CGC  ATC  TCA  AAC  CAA  TTG  TCG  GAA  ACT  CAG  TTA  AAG  TAT  CAC        270
Lys  Arg  Ile  Ser  Asn  Gln  Leu  Ser  Glu  Thr  Gln  Leu  Lys  Tyr  His
          55                        60                        65

TGC  TGC  AAG  AAG  AAC  CTG  TGT  AAT  GTT  AAG  GAA  GTG  CTT  GAA  AAT        315
Cys  Cys  Lys  Lys  Asn  Leu  Cys  Asn  Val  Lys  Glu  Val  Leu  Glu  Asn
```

```
                        70                          75                           80
GGT  GGG  ACA  ACC  TTA  TCA  AAG  AAA  ACA  ATT  CTT  CTG  CTG  GTG  ACC         360
Gly  Gly  Thr  Thr  Leu  Ser  Lys  Lys  Thr  Ile  Leu  Leu  Leu  Val  Thr
                         85                          90                          95

CCG  TTT  CTG  GCA  GCA  GCC  TGG  AGC  CGT  CAT  CCC  TAA                        396
Pro  Phe  Leu  Ala  Ala  Ala  Trp  Ser  Arg  His  Pro
                    100                        105
```

( 2 ) INFORMATION FOR SEQ ID NO:7:

( i ) SEQUENCE CHARACTERISTICS:
        ( A ) LENGTH: 387 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: OWMCIP full coding cDNA ( i i i ) HYPOTHETICAL: No ( i v ) ANTI-SENSE: No ( v i ) ORIGINAL SOURCE:
        ( A ) ORGANISM: Aotus trivirgatus
        ( H ) CELL LINE: OMK (ATCC CRL 1556)

( x i ) SEQUENCE DESCRIPTION: SEQ ID NO:7:

```
ATG  GGA  ATT  CAA  GGA  GGG  TCT  GTC  CTG  TTT  GGG  CTG  CTG  CTC  GTC         45
Met  Gly  Ile  Gln  Gly  Gly  Ser  Val  Leu  Phe  Gly  Leu  Leu  Leu  Val
-25                      -20                        -15

CTG  GCT  GTC  TTC  TGC  CAT  TCA  GGT  AAT  AGC  CTG  CAG  TGC  TAC  AGC         90
Leu  Ala  Val  Phe  Cys  His  Ser  Gly  Asn  Ser  Leu  Gln  Cys  Tyr  Ser
-10                      -5                          1                     5

TGT  CCT  TAC  CCA  ACC  ACT  CAG  TGC  ACT  ATG  ACC  ACC  AAC  TGT  ACA         135
Cys  Pro  Tyr  Pro  Thr  Thr  Gln  Cys  Thr  Met  Thr  Thr  Asn  Cys  Thr
                         10                         15                      20

TCT  AAT  CTT  GAT  TCG  TGT  CTC  ATT  GCC  AAA  GCC  GGG  TCA  CGA  GTA         180
Ser  Asn  Leu  Asp  Ser  Cys  Leu  Ile  Ala  Lys  Ala  Gly  Ser  Arg  Val
                         25                         30                      35

TAT  TAC  CGG  TGT  TGG  AAG  TTT  GAG  GAT  TGC  ACT  TTC  AGC  CGC  GTT         225
Tyr  Tyr  Arg  Cys  Trp  Lys  Phe  Glu  Asp  Cys  Thr  Phe  Ser  Arg  Val
                         40                         45                      50

TCA  AAC  CAA  TTG  TCT  GAA  AAT  GAG  TTA  AAG  TAT  TAC  TGC  TGC  AAG         270
Ser  Asn  Gln  Leu  Ser  Glu  Asn  Glu  Leu  Lys  Tyr  Tyr  Cys  Cys  Lys
                         55                         60                      65

AAG  AAC  CTG  TGT  AAC  TTT  AAT  GAA  GCG  CTT  AAA  AAT  GGT  GGG  ACA         315
Lys  Asn  Leu  Cys  Asn  Phe  Asn  Glu  Ala  Leu  Lys  Asn  Gly  Gly  Thr
                         70                         75                      80

ACC  TTA  TCA  AAG  AAA  ACA  GTC  CTC  CTG  CTG  GTG  ATC  CCA  TTT  CTG         360
Thr  Leu  Ser  Lys  Lys  Thr  Val  Leu  Leu  Leu  Val  Ile  Pro  Phe  Leu
                         85                         90                      95

GTA  GCA  GCC  TGG  AGC  CTT  CAT  CCC  TAA                                       387
Val  Ala  Ala  Trp  Ser  Leu  His  Pro
                    100
```

( 2 ) INFORMATION FOR SEQ ID NO:8:

( i ) SEQUENCE CHARACTERISTICS:
        ( A ) LENGTH: 387 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: MARCIP full coding cDNA ( i i i ) HYPOTHETICAL: No ( i v ) ANTI-SENSE: No ( v i ) ORIGINAL SOURCE:
    ( A ) ORGANISM: Saguinus nigricollis
    ( H ) CELL LINE: 1283.Lu (ATCC CRL 6297)

( x i ) SEQUENCE DESCRIPTION: SEQ ID NO:8:

```
ATG  GGA  ATC  CAA  GGA  GGG  TCT  GTC  CTG  TTT  GGG  CTG  CTG  CTC  ATC          45
Met  Gly  Ile  Gln  Gly  Gly  Ser  Val  Leu  Phe  Gly  Leu  Leu  Leu  Ile
-25            -20                      -15

CTG  GCT  GTC  TTC  TGC  CAT  TCA  GGT  CAT  AGC  CTG  CAG  TGC  TAC  AGC          90
Leu  Ala  Val  Phe  Cys  His  Ser  Gly  His  Ser  Leu  Gln  Cys  Tyr  Ser
-10            -5                         1                          5

TGT  CCT  TAC  TCA  ACC  GCT  CGG  TGC  ACT  ACG  ACC  ACC  AAC  TGT  ACA         135
Cys  Pro  Tyr  Ser  Thr  Ala  Arg  Cys  Thr  Thr  Thr  Thr  Asn  Cys  Thr
                10                       15                         20

TCT  AAT  CTT  GAT  TCA  TGT  CTC  ATT  GCC  AAA  GCC  GGG  TTA  CGA  GTA         180
Ser  Asn  Leu  Asp  Ser  Cys  Leu  Ile  Ala  Lys  Ala  Gly  Leu  Arg  Val
                25                       30                         35

TAT  TAC  CGG  TGT  TGG  AAG  TTT  GAG  GAT  TGC  ACT  TTC  AGA  CAA  CTT         225
Tyr  Tyr  Arg  Cys  Trp  Lys  Phe  Glu  Asp  Cys  Thr  Phe  Arg  Gln  Leu
                40                       45                         50

TCA  AAC  CAA  TTG  TCG  GAA  AAT  GAG  TTA  AAG  TAT  CAC  TGC  TGC  AGG         270
Ser  Asn  Gln  Leu  Ser  Glu  Asn  Glu  Leu  Lys  Tyr  His  Cys  Cys  Arg
                55                       60                         65

GAG  AAC  CTG  TGT  AAC  TTT  AAC  GGA  ATA  CTT  GAA  AAT  GGT  GGG  ACA         315
Glu  Asn  Leu  Cys  Asn  Phe  Asn  Gly  Ile  Leu  Glu  Asn  Gly  Gly  Thr
                70                       75                         80

ACC  TTA  TCA  AAG  AAA  ACA  GTT  CTT  CTG  GTG  ACC  CCT  TTT  CTG              360
Thr  Leu  Ser  Lys  Lys  Thr  Val  Leu  Leu  Val  Thr  Pro  Phe  Leu
                85                       90                         95

GCA  GCA  GCC  TGG  AGC  CTT  CAT  CCC  TAA                                        387
Ala  Ala  Ala  Trp  Ser  Leu  His  Pro
               100
```

( 2 ) INFORMATION FOR SEQ ID NO:9:

( i ) SEQUENCE CHARACTERISTICS:
        ( A ) LENGTH: 1039 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: HVS-15 full length cDNA ( i i i ) HYPOTHETICAL: No ( i v ) ANTI-SENSE: No ( v i ) ORIGINAL SOURCE:
        ( A ) ORGANISM: Herpesvirus saimiri ( x ) PUBLICATION INFORMATION:
        ( A ) AUTHORS: Albrecht, J.C.
                Nicholas, J.
                Cameron, K.R.
                Newman, C.
                Fleckenstein, B.
                Honess, R.W.
        ( B ) TITLE: Herpesvirus saimiri has a gene specifying
                a homologue of the cellular membrane
                glycoprotein CD59.
        ( C ) JOURNAL: Virology
        ( D ) VOLUME: 190
        ( F ) PAGES: 527-530
        ( G ) DATE: 1992

( x i ) SEQUENCE DESCRIPTION: SEQ ID NO:9:

| | | | | | | | | | | |
|---|---|---|---|---|---|---|---|---|---|---|
| AAGCTTCTAT | TTATACTACA | TTAGAGGCAT | TTTTTCAAAA | GCAAAAATGC | | | | | | 50 |
| CTCTAATTAT | ATACACTGTA | CTATTTACCT | CTATTACACA | TTTTCTATTT | | | | | | 100 |
| TAAGTCTGAT | AGTGATTAAT | CAAGAAAAAA | GTTGTGGTT | CTCAGGGGAT | | | | | | 150 |
| TAGTTCACAA | GCTGTCTGAG | GTTAAGGGTG | TTTCTTTGGC | ACTGACACAG | | | | | | 200 |
| AAGTTGCTAT | AAGAATTGAA | GCTTGCTTTA | CAAAAAGTTA | CTTGTGATTA | | | | | | 250 |

```
ATTACTATAA CAAGAAAGGT A ATG TAT ATT TTG TTT ACG TTG GTA                    295
                        Met Tyr Ile Leu Phe Thr Leu Val
                                        -15

CTG ACT TTT GTT TTT TGC AAG CCA ATA CAC AGC TTG CAA TGC                    337
Leu Thr Phe Val Phe Cys Lys Pro Ile His Ser Leu Gln Cys
    -10              -5                          1

TAC AAC TGT TCT CAC TCA ACT ATG CAG TGT ACT ACA TCT ACT                    379
Tyr Asn Cys Ser His Ser Thr Met Gln Cys Thr Thr Ser Thr
        5               10                  15

AGT TGT ACA TCT AAT CTT GAC TCT TGT CTC ATT GCT AAA GCT                    421
Ser Cys Thr Ser Asn Leu Asp Ser Cys Leu Ile Ala Lys Ala
        20              25                  30

GGG TCA GGA GTA TAT TAC AGG TGT TGG AAG TTT GAT GAC TGT                    463
Gly Ser Gly Val Tyr Tyr Arg Cys Trp Lys Phe Asp Asp Cys
        35              40                  45

AGC TTT AAA CGT ATC TCA AAT CAA TTG TCT GAA ACA CAG TTA                    505
Ser Phe Lys Arg Ile Ser Asn Gln Leu Ser Glu Thr Gln Leu
        50              55

AAG TAT CAT TGT TGT AAG AAG AAC TTG TGT AAT GTG AAC AAA                    547
Lys Tyr His Cys Cys Lys Lys Asn Leu Cys Asn Val Asn Lys
60          65                  70

GGG ATT GAA AAT ATT AAA AGA ACA ATA TCA GAT AAA GCT CTT                    589
Gly Ile Glu Asn Ile Lys Arg Thr Ile Ser Asp Lys Ala Leu
    75              80                  85

TTA CTA TTA GCA TTG TTT TTA GTA ACT GCT TGG AAC TTT CCT                    631
Leu Leu Leu Ala Leu Phe Leu Val Thr Ala Trp Asn Phe Pro
        90              95                  100

CTT TAAAAG TCAACAACAA AACTATATTG TAACATTTAT TTTTGTGTAG                     680
Leu
```

| | | | | | |
|---|---|---|---|---|---|
| CTTATTTGTA | TTGCTATTAC | AAGTTAAAAT | ATTGTGTTTT | TTAAACTATA | 730 |
| ATTTTAAAA | AGATAAAATG | AGATGTAGTA | TACTACATAG | TCAAAATTAA | 780 |
| AGTGCTAAAT | ATTATTAGCA | ATTTTTTATC | AACAACGCAA | ATAAAAGTTA | 830 |
| AGCTACTTTA | TTTTTTCTGT | TATCTAAATC | ATTACGCGCT | TCTTAGCATG | 880 |
| TGTTAAAAGT | TTTATGTGAT | TTTATTCTTA | CATATATAAA | GCTAAATTTT | 930 |
| AAAGCAAATT | ATCAGTAGCA | TCTTATCTTC | TAATCTGTAC | AGACCTATAT | 980 |
| AATATGGGAT | TATCCTTAAG | AAAAAACAGC | GGAGAAAAAG | AAAACACAGT | 1030 |
| GCCAAGCTT | | | | | 1039 |

( 2 ) INFORMATION FOR SEQ ID NO:10:

( i ) SEQUENCE CHARACTERISTICS:
        ( A ) LENGTH: 33 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: Oligo A – 5'primer ( i i i ) HYPOTHETICAL: No ( i v ) ANTI-SENSE: No ( x i ) SEQUENCE DESCRIPTION: SEQ ID NO:10:

CGCTGGGCGT AGCGTCGACT CGGCGGAGTC CCG    33

( 2 ) INFORMATION FOR SEQ ID NO:11:

( i ) SEQUENCE CHARACTERISTICS:
        ( A ) LENGTH: 38 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: Oligo B -- 3'primer ( i i i ) HYPOTHETICAL: No ( i v ) ANTI-SENSE: Yes ( x i ) SEQUENCE DESCRIPTION: SEQ ID NO:11:

GCCCATGGAT CCTAGCGTCT AAAGCAAACC TGTCAACG    38

( 2 ) INFORMATION FOR SEQ ID NO:12:

( i ) SEQUENCE CHARACTERISTICS:
        ( A ) LENGTH: 34 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: Oligo 54 -- 5'primer ( i i i ) HYPOTHETICAL: No ( i v ) ANTI-SENSE: No ( x i ) SEQUENCE DESCRIPTION: SEQ ID NO:12:

GAAGAGTTCT GCAGAATCGT AGCTGCGAGG TGCC    34

( 2 ) INFORMATION FOR SEQ ID NO:13:

( i ) SEQUENCE CHARACTERISTICS:
        ( A ) LENGTH: 47 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: Oligo 55 -- 3'primer ( i i i ) HYPOTHETICAL: No ( i v ) ANTI-SENSE: Yes ( x i ) SEQUENCE DESCRIPTION: SEQ ID NO:13:

CCACGTGCTG CAGTCCTCCA CCTCCTCCTC TGCATTCAGG TGGTGGG    47

( 2 ) INFORMATION FOR SEQ ID NO:14:

( i ) SEQUENCE CHARACTERISTICS:
        ( A ) LENGTH: 25 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: Oligo 5 -- 5'primer ( i i i ) HYPOTHETICAL: No 5,627,264

47

48

-continued ( i v ) ANTI-SENSE: No ( x i ) SEQUENCE DESCRIPTION: SEQ ID NO:14:

GGAAGAGGAT CCTGGGCGCC GCAGG                    25

( 2 ) INFORMATION FOR SEQ ID NO:15:

( i ) SEQUENCE CHARACTERISTICS:
    ( A ) LENGTH: 44 bases
    ( B ) TYPE: Nucleic Acid
    ( C ) STRANDEDNESS: Single
    ( D ) TOPOLOGY: Linear ( i i ) MOLECULE TYPE: Other nucleic acid
    ( A ) DESCRIPTION: Oligo 53 -- 3'primer ( i i i ) HYPOTHETICAL: No ( i v ) ANTI-SENSE: Yes ( x i ) SEQUENCE DESCRIPTION: SEQ ID NO:15:

GGTCTTCGGC CGCTCCACCT CCCCCACCAT TTTCAAGCTG TTCG           44

( 2 ) INFORMATION FOR SEQ ID NO:16:

( i ) SEQUENCE CHARACTERISTICS:
    ( A ) LENGTH: 39 bases
    ( B ) TYPE: Nucleic Acid
    ( C ) STRANDEDNESS: Single
    ( D ) TOPOLOGY: Linear ( i i ) MOLECULE TYPE: Other nucleic acid
    ( A ) DESCRIPTION: Oligo 175 -- 5'primer ( i i i ) HYPOTHETICAL: No ( i v ) ANTI-SENSE: No ( x i ) SEQUENCE DESCRIPTION: SEQ ID NO:16:

CCCCAAATAA AGGAAGTGGA ACCACTTCAG GTACTACCC              39

( 2 ) INFORMATION FOR SEQ ID NO:17:

( i ) SEQUENCE CHARACTERISTICS:
    ( A ) LENGTH: 44 bases
    ( B ) TYPE: Nucleic Acid
    ( C ) STRANDEDNESS: Single
    ( D ) TOPOLOGY: Linear ( i i ) MOLECULE TYPE: Other nucleic acid
    ( A ) DESCRIPTION: Oligo 176 -- 3'primer ( i i i ) HYPOTHETICAL: No ( i v ) ANTI-SENSE: Yes ( x i ) SEQUENCE DESCRIPTION: SEQ ID NO:17:

GGCTAAGTCA GCAAGCCCAT GGTTACTAGC GTCCCAAGCA AACC           44

( 2 ) INFORMATION FOR SEQ ID NO:18:

( i ) SEQUENCE CHARACTERISTICS:
    ( A ) LENGTH: 40 bases
    ( B ) TYPE: Nucleic Acid
    ( C ) STRANDEDNESS: Single
    ( D ) TOPOLOGY: Linear ( i i ) MOLECULE TYPE: Other nucleic acid
    ( A ) DESCRIPTION: Oligo 173

( i i i ) HYPOTHETICAL: No

```
        ( i v ) ANTI-SENSE: No ( x i ) SEQUENCE DESCRIPTION: SEQ ID NO:18:

TGCACGGATC  CATGACCGTC  GCGCGGCCGA  GCGTGCCCGC                    40

( 2 ) INFORMATION FOR SEQ ID NO:19:

( i ) SEQUENCE CHARACTERISTICS:
                ( A ) LENGTH: 34 bases
                ( B ) TYPE: Nucleic Acid
                ( C ) STRANDEDNESS: Single
                ( D ) TOPOLOGY: Linear ( i i ) MOLECULE TYPE: Other nucleic acid
                ( A ) DESCRIPTION: Oligo 174

( i i i ) HYPOTHETICAL: No ( i v ) ANTI-SENSE: Yes ( x i ) SEQUENCE DESCRIPTION: SEQ ID NO:19:

GGGCACGCTC  GGCCGCGCGA  CGGTCATGGA  TCCG                          34
```

CHIMERIC COMPLEMENT INHIBITOR PROTEINS

FIELD OF THE INVENTION

The present invention relates to chimeric complement inhibitor proteins (cCIPs) that contain functional domains from two complement inhibitor proteins (CIPs), the functional domain from one CIP having C3 inhibitory activity and the functional domain from the other CIP having C5b-9 inhibitory activity. More particular, the invention relates to such chimeric proteins wherein a domain having C3 inhibitory activity is amino terminal to a domain having C5b-9 inhibitory activity.

BACKGROUND OF THE INVENTION

I. The Complement System

The complement system is a complex interaction of at least 25 plasma proteins and membrane cofactors which act in a multistep, multiprotein cascade sequence in conjunction with other immunological systems of the body to defend against intrusion of foreign cells and viruses. Complement proteins represent up to about 10% of globulins in normal serum of humans and other vertebrates. Complement components achieve their immune defensive functions by interacting in a series of intricate but precise enzymatic cleavage and membrane binding events. The resulting complement cascade leads to the production of products with opsonic, immunoregulatory, and lytic functions.

There are two main routes of complement activation: the classical pathway and the alternative pathway. These pathways share many components, and while they differ in their initial steps, they converge and share the same "terminal complement" components responsible for the activation, attack, and/or destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. The active protease, which is referred to as C3 convertase, comprises complement components C2bC4b for the classical pathway and complement components C3bBb for the alternative pathway.

C3a is an anaphylotoxin that can induce degranulation of mast cells, resulting in the release of histamine and other mediators of inflammation. C3b has multiple functions. As opsonin, it binds to bacteria, viruses and other cells and particles and tags them for removal from the circulation. C3b can also form a complex with other components unique to each pathway to form classical or alternative C5 convertase, which cleaves C5 into C5a (another anaphylatoxin), and C5b.

C5a, like C3a, is a potent anaphylatoxin which can cause the activation of granulocytes and platelets. Additionally, C5a is a chemoattractant for neutrophils and also mediates mast cell histamine release and resulting smooth muscle contraction. C5b, on the other hand, combines with C6, C7, and C8 to form the C5b-8 complex at the surface of the target cell. Upon binding of C9 the membrane attack complex (MAC, C5b-9) is formed. When sufficient numbers of MACs insert into target cell membranes, the openings they create mediate rapid lysis of the target cells. Lower, non-lytic concentrations of MACs can produce other effects. In particular, membrane insertion of small numbers of the C5b-9 complexes into endothelial cells and platelets can cause potentially deleterious cell activation. In some cases activation may precede cell lysis.

Control of the complement system is necessary in order to prevent destruction of autologous cells. Since 1900 it has been known that complement-mediated cytolysis is not efficient when the complement and the target cells are from the same species. (Bordet, 1900.) Studies on the susceptibility of non-human cells to complement-mediated lysis have shown that such cells are readily lysed by human complement while they are generally resistant to lysis by complement derived from the same species. (Houle et al., 1988). This phenomenon is referred to in the art as "homologous species restriction of complement-mediated lysis." The mechanism by which such restriction takes place has been at least partially revealed by a series of experiments in which complement regulatory proteins have been identified that serve to protect cells from homologous complement-mediated damage. (Rollins et al., 1991).

II. C3 Inhibitor Proteins

A family of cell-surface proteins with shared structural features has been described each of whose actions impact on C3b.

Decay accelerating factor (DAF or CD55) exists on all cells, including red blood cells. DAF is a single chain, 70 kDa glycoprotein that is linked to the cell membrane via a glycophosphatidyinositol (GPI) moiety which inserts into the outer leaflet of the plasma membrane bilayer.

DAF regulates complement activation at the C3 convertase stage by preventing the assembly of the C3 convertases of both the classical and alternative pathways (Medof et al., 1984; Fujita et al., 1987). Thus, DAF prevents the formation of the anaphylactic cleavage fragments C3a and C5a, in addition to inhibiting amplification of the complement cascade on host cell membranes.

DAF has been shown to act exclusively in an intrinsic manner on cells, protecting only the cell on whose surface it resides while having no effect on neighboring cells. After extraction from human red blood cells, DAF reincorporates into cell membranes and is biologically active. Both membrane and secreted forms of DAF have been identified and their cDNAs have been cloned and characterized (Moran et al., 1992).

The nucleotide and amino acid sequences for human DAF are set forth in the Sequence Listings as SEQ ID NO:1.

Membrane cofactor protein (MCP or CD46) exists on all cells except red blood cells. MCP is a type I transmembrane glycoprotein that binds to C3b. MCP acts as a cofactor in the factor I-mediated cleavage of C3b and C4b deposited on self tissue. Therefore, the presence of bound MCP activates molecules that cleave C3b into inactive fragments, preventing the potentially cytolytic accumulation of C3b. Nucleotide and amino acid sequences for MCP can be found in Lublin, et al., 1988.

Complement receptor 1 (CR1 or CD35) is found on erythrocytes as well as a select group of leukocytes, including lymphocytes, neutrophils, and eosinophils. CR1 is a 190–280 kDa transmembrane protein that triggers the proteolytic degradation of membrane bound C3b molecules with which it comes in contact. It also promotes the clearance of immune complexes. Nucleotide and amino acid sequences for CR1 can be found in Wong, et al., 1985.

Factor H and C4b-binding protein each inhibit the activity of alternative pathway C3 convertase. Nucleotide and amino acid sequences for factor H can be found in Ripoche, et al., 1988; nucleotide and amino acid sequences for C4b-binding protein can be found in Chung, et al., 1985.

The genes encoding all of these C3 inhibitory proteins have been mapped to the long arm of chromosome 1, band 1q32, and constitute a locus designated the RCA (Regulators of Complement Activity) gene cluster. Notable in the molecular structure of these C3 inhibitory proteins is a common structural motif of approximately 60 amino acids designated the SCR (short consensus repeat), which is normally present in multiple copies that are not necessarily identical. See Perkins et al. 1988; Coyne, et al., 1992.

The SCR motif of these C3 inhibitory proteins has four conserved cysteine residues and conserved tryptophan, glycine, and phenylalanine/tyrosine residues. The SCRs are usually followed by a long serine/threonine rich region.

In DAF and MCP, the SCRs are known to encode functional domains necessary for full complement inhibitory activity (Adams, et al., 1991). DAF is composed of 4 SCRs juxtaposed to a serine/threonine rich region on the carboxyl terminal side of the SCRs. Most, if not all, of the functional domains are reported to reside in SCRs 2 through 4 (Coyne et al., 1992). In SEQ ID NO:1, the 4 SCRs of DAF comprise amino acid 1 through amino acid 61 (SCR 1), amino acid 62 through amino acid 125 (SCR 2), amino acid 126 through amino acid 187 (SCR 3), and amino acid 188 through amino acid 250 (SCR 4), Lublin, et al., 1989.

The phrase "C3 inhibitory activity" is used herein to describe the effects of C3 inhibitor molecules of the foregoing types on the complement system and thus includes activities that lead to disruption of the C3 convertase complex and/or activities that are responsible for the degradation of C3b.

III. C5b-9 Inhibitor Proteins

The archetypical C5b-9 inhibitor protein is the human glycoprotein known as CD59. The nucleotide and amino acid sequences for human CD59 are set forth in the Sequence Listings as SEQ ID NO:2.

CD59 is found associated with the membranes of cells including human erythrocytes, lymphocytes, and vascular endothelial cells. It serves to prevent assembly of functional MACs and thus protects cells from complement-mediated activation and/or lysis. CD59 has an apparent molecular mass of 18–21 kilodaltons (kD) and, like DAF, is tethered to the outside of the cell membrane by a GPI anchor. See, for example, Sims et al., U.S. Pat. No. 5,135,916.

CD59 appears to function by competing with C9 for binding to C8 in the C5b-8 complex, thereby decreasing the formation of the C5b-9 membrane attack complex. (Rollins et al., 1990.) CD59 thus acts to reduce both cell activation and cell lysis by terminal complement MACs. This activity of CD59 is for the most part species-restricted, most efficiently blocking the formation of MACs under conditions where C8 and C9 are derived from homologous (i.e., human) serum. (Venneker et al., 1992.)

The assimilation of purified CD59 into the plasma membrane of non-human erythrocytes (which appear to be protected from homologous complement lysis by the action of their own cell surface complement inhibitor proteins) and oligodendrocytes (brain cells which are believed to be protected less, if at all, by cell surface proteins, but may be protected in vivo by the blood brain barrier) has shown that CD59 can protect these cells from lysis mediated by human complement. (Rollins, et al., 1990; Rollins, et al., 1991; Stefanova, et al., 1989; Meri, et al., 1990; Whitlow, et al., 1990; Okada, et al., 1989; and Wing, et al., 1992).

cDNAs encoding CD59 have been cloned and the structure of the CD59 gene has been characterized (Davies, et al., 1989; Okada, et al., 1989; Philbrick, et al., 1990; Sawada, et al., 1990; and Tone, et al., 1992). Non-human mammalian cells transfected with the cloned CD59 cDNA, and thereby expressing the human CD59 protein on their cell surfaces, have been shown to gain resistance to complement-mediated cell lysis (Zhao, et al., 1991; and Walsh, et al., 1991).

CD59 has been reported to be structurally related to the murine Ly-6 antigens (Philbrick, et al., 1990; and Petranka, et al., 1992). The genes encoding these antigens, also known as T-cell activating proteins, are members of the Ly-6 multigene family, and include Ly-6A.2, Ly-6B.2, Ly-6C.1, Ly-6C.2, and Ly-6E.1. The gene encoding the murine thymocyte B cell antigen ThB is also a member of this family (Shevach, et al. 1989; and Gumley, et al., 1992).

A distinguishing feature of the amino acid sequences of the proteins of the Ly-6 family is the arrangement of their cysteine residues. Cysteine residues of many proteins form a structural element referred to in the art as a "cysteine backbone." In those proteins in which they occur, cysteine backbones play essential roles in determining the three dimensional folding, tertiary structure, and ultimate function of the protein molecule.

The proteins of the Ly-6 multigene family, as well as several other proteins share a particular cysteine backbone structure referred to herein as the "Ly-6 motif". For example, the human urokinase plasminogen activator receptor (uPAR; Roldan, et al., 1990) and one of several squid glycoproteins of unknown function (Sgp2; Williams, et al., 1988) contain the Ly-6 motif.

Subsets of proteins having the Ly-6 motif can be identified by the presence of conserved amino acid residues immediately adjacent to the cysteine residues. Such conservation of specific amino acids within a subset of proteins can be associated with specific aspects of the folding, tertiary structure, and ultimate function of the proteins. These conserved patterns are most readily perceived by aligning the sequences of the proteins so that the cysteine residues are in register.

As discussed fully in copending, commonly assigned, U.S. patent application Ser. No. 08/105,735, filed Aug. 11, 1993, by William L. Fodor, Scott Rollins, Russell Rother, and Stephen P. Squinto, and entitled "Complement Inhibitor Proteins of Non-human Primates", the relevant portions of which are incorporated herein by reference, and in Rother, et al., 1994, a series of non-human primate C5b-9 inhibitory proteins have been identified which are characterized by a cysteine backbone structure which defines a specific subset of the general Ly-6 motif.

Specifically, these non-human primate CIPs include polypeptides comprising a cysteine backbone with a Ly-6 motif characterized by the formula:

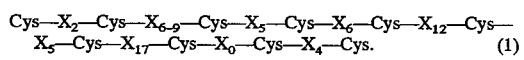
$$\text{Cys}-X_2-\text{Cys}-X_{6-9}-\text{Cys}-X_5-\text{Cys}-X_6-\text{Cys}-X_{12}-\text{Cys}-X_5-\text{Cys}-X_{17}-\text{Cys}-X_0-\text{Cys}-X_4-\text{Cys}. \qquad (1)$$

In addition, the non-human primate C5b-9 inhibitory proteins include amino acid sequences conforming to the following formula:

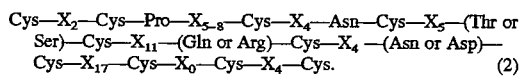
$$\text{Cys}-X_2-\text{Cys}-\text{Pro}-X_{5-8}-\text{Cys}-X_4-\text{Asn}-\text{Cys}-X_5-(\text{Thr or Ser})-\text{Cys}-X_{11}-(\text{Gln or Arg})-\text{Cys}-X_4-(\text{Asn or Asp})-\text{Cys}-X_{17}-\text{Cys}-X_0-\text{Cys}-X_4-\text{Cys}. \qquad (2)$$

In both formulas, the X in $X_n$ indicates a peptide containing any combination of amino acids, the n in $X_n$ represents the length in amino acid residues of the peptide, and each X at any position can be the same as or different from any other X of the same length in any other position.

As discussed fully in commonly assigned, copending PCT application Ser. No. PCT/US 93/00672, filed Jan. 12, 1993, by Bernhard Fleckenstein and Jens-Christian Albrecht, and entitled "Complement Regulatory Proteins of *Herpesvirus Saimiri*", the relevant portions of which are incorporated herein by reference, and in Albrecht, et al., 1992, a protein of the herpesvirus saimiri having C5b-9 inhibitory activity has been discovered (referred to herein as "HVS-15"). This viral protein has the Ly-6 motif which is characteristic of the non-human primate C5b-9 inhibitory proteins discussed above, i.e., its structure is described by formulas (1) and (2) above.

The phrase "C5b-9 inhibitory activity" is used herein to describe the effects of C5b-9 inhibitor molecules of the foregoing types on the complement system and thus includes activities that lead to inhibition of the cell activating and/or lytic function of the membrane attack complex (MAC).

V. Complement Associated Pathologies

Human studies and studies using animal models of human disorders have implicated CIPs in the pathologies associated with a number of disorders, including the following.

Transplantation: Intrinsic activation of complement attack via the alternative pathway during storage of donor organs is responsible for certain problems associated with organ transplantation which arise as a result of endothelial cell stimulation and/or lysis by the C5b-9 MAC (Brasile, et al. 1985). Ex vivo complement attack leads to reduced vascular viability and reduced vascular integrity when stored organs are transplanted, increasing the likelihood of transplant rejection.

Ten percent of allogeneic transplanted kidneys with HLA-identical matches are rejected by in vivo immunologic mechanisms (Brasile, et al. 1987). In 78% of the patients who reject organs under these conditions, cytotoxic antibodies binding to molecules on the surfaces of vascular endothelial cells are seen (Brasile, et al., 1987). Such antibody cytotoxicity is mediated by complement attack, and is responsible for the rejection of transplanted solid organs including kidneys and hearts (Brasile, et al., 1987; Brasile et al., 1985). Antibody primed, complement-mediated rejection is usually rapid and irreversible, a phenomenon referred to as hyperacute rejection.

In the xenogeneic setting, as when non-human organs are transplanted into human patients, activation of complement attack by antibodies directed against molecules on the surfaces of endothelial cells lining the vessels of the donor organ is almost always observed. The prevalence of such xenoreactive antibodies accounts for the nearly universal occurrence of hyperacute rejection of xenografts (Dalmasso, et al., 1992). Old world primates, including humans, have high levels of preexisting circulating "natural" antibodies that predominantly recognize carbohydrate determinants expressed on the surface of xenogeneic cells from discordant species. Recent evidence indicates that most of these antibodies react with galactose in an α1-3 linkage with galactose.(Gal(α1-3)Gal) (Sandrin, et al., 1993).

Old world primates lack the appropriate functional α-1, 3-galactose transferase and thus do not express this carbohydrate epitope. Therefore, following transplantation of a vascularized xenogeneic donor organ, these high-titer antibodies bind to the Gal(α1-3)Gal epitope on the vascular endothelium and activate the recipient's complement through the classical pathway. The massive inflammatory response that ensues from activation of the complement cascade leads to the destruction of the donor organ within minutes to hours.

Xenoreactive antibodies are not exclusively responsible for hyperacute rejection of discordant organs in all cases. For example, erythrocytes from some species can activate human complement via the alternative pathway and newborn piglets raised to be free of preformed antibodies reject xenografts almost immediately. It is therefore likely that in some species combinations, activation of the alternative complement pathway contributes to graft rejection.

Endogenously-expressed, membrane-associated complement inhibitory proteins normally protect endothelial cells from autologous complement. However, the species restriction of complement inhibitors makes them relatively ineffective with respect to regulating discordant xenogeneic serum complement. The lack of effective therapies aimed at eliminating this antibody and complement-mediated hyperacute rejection presents a major barrier to the successful transplantation of discordant animal organs into human recipients.

Recently, a report on a baboon-to-human liver transplant has been published in which the xenogeneic donor organ failed to exhibit signs of hyperacute rejection (Starzl, et al., 1993). The low levels of anti-baboon antibodies likely to be present in human blood make hyperacute responses less likely. However, it is believed that recently discovered baboon CIPs, which have been shown to be related to CD59 and to be effective against human complement, also played a role in maintaining the integrity of this xenotransplanted organ. (See U.S. patent application Ser. No. 08/105,735, referred to above.)

The lack of hyperacute rejection seen in the baboon to human xenotransplant discussed above suggests that complement inhibitor proteins effective against human complement may, in combination with other anti-rejection strategies, allow safe and effective xenotransplantation of transgenic animal organs expressing such proteins into human patients.

Paroxysmal Nocturnal Hemoglobinuria: A complement mediated disease that involves the alternative pathway of complement activation is the stem cell disorder paroxysmal nocturnal hemoglobinuria. Complement inhibitory proteins, including CD59, are absent from the membranes of the most hemolytically sensitive erythrocytes found in patients with this disease. The lack of these proteins is thought to potentiate the complement-mediated lysis of red blood cells that characterizes the disease (see Venneker et al., 1992). The use of chimeric terminal complement inhibitor proteins in the treatment of PNH cells is discussed in copending, commonly assigned, U.S. patent application Ser. No. 08/206, 189, entitled "Method for the Treatment of Paroxysmal Nocturnal Hemoglobinuria," which is being filed concurrently herewith in the names of Russell Rother, Scott Rollins, Seth A. Fidel, and Stephen P. Squinto.

VI. CIPs with Modified Membrane Anchors

Work has been performed in which CIPs with modified membrane anchors have been generated in order to study the functional consequences of altering the means of attachment of GPI-anchored proteins to the outer cell surface. In these studies, the native cell surface anchoring of the CIPs has been varied from their natural GPI anchors by substitution of other anchoring moieties (Su, et al., 1991; and Lublin, et al., 1991).

For example, derivatives of DAF, containing amino acids 1–304 of DAF fused to the transmembrane domain of MCP (i.e., amino acids 270–350 of MCP) or to the transmembrane domain of the human major histocompatibility protein HLA-B44 (i.e., amino acids 262–338 of HLA-B44) have been reported to retain levels of function equivalent to native DAF (Lublin, et al., 1991).

Derivatives of CD59, containing amino acids 1–77 of CD59 fused to the transmembrane domain of MCP (i.e., amino acids 270–350 of MCP) have been shown to retain levels of function equivalent to native CD59 in copending, commonly assigned, U.S. patent application Ser. No. 08/205,720, entitled "Terminal Complement Inhibitor Fusion Genes and Proteins," which is being filed concurrently herewith in the names of Russell Rother, Scott Rollins, and Stephen P. Squinto.

SUMMARY OF THE INVENTION

In view of the foregoing, it is an object of the present invention to provide novel chimeric proteins for use in inhibiting the complement system. To achieve this and other objects, the invention provides cCIPs that contain functional domains of two CIPs, one of the functional domains having C3 inhibitory activity and the other functional domain having C5b-9 inhibitory activity, where the C3 inhibitory activity is amino terminal to the C5b-9 inhibitory activity. In the preferred forms of the invention, the C3 and C5b-9 inhibitory activities are directed against the human complement system.

The invention also provides 1) nucleic acid molecules encoding such cCIPs, 2) transgenic cells, tissues, organs, and animals containing such nucleic acid molecules, 3) expression vectors containing the nucleic acid molecules, and 4) host cells containing the expression vectors.

Significantly, as a result of their structure, i.e., the ordering of the inhibitory activities within the chimeric molecule, the cCIPs of the invention simultaneously exhibit both C3 inhibitory activity and C5b-9 inhibitory activity, a result not previously achieved in the art.

In accordance with the invention, these chimeric proteins and the polynucleotides encoding them may be used as components of therapeutic agents for the prevention and/or treatment of complement-mediated pathologies. The protection from complement attack offered by the cCIPs of the invention can be provided via gene transfer for the therapeutic prevention of pathologic complement attack in, for example, transplantation. In a preferred form of such therapy, the expression of the cCIP can be directed to the surfaces of cells of non-human animal organs in order to protect such organs from complement attack upon transplantation into a human patient.

The invention is particularly advantageous in the production of transgenic animals. Microinjection of recombinant DNA into the pronuclei of animal ova has become a routine procedure for generating transgenic animals. However, since this technology is dependent on random integration of DNA, it is difficult to achieve targeted cellular expression of two distinct heterologous proteins by the simultaneous microinjection of their respective DNAs, as would be required if C3 inhibitory activity and C5b-9 inhibitory activity were to be achieved through the use of individual CIPs. The present invention overcomes this technological hurdle since it provides a novel single gene which encodes both C3 and C5b-9 inhibitory activity in a single protein.

Further, since many CIPs, in particular, DAF and CD59, are anchored to the plasma membrane via glycophospholipid moieties (GPI anchors), it is additionally difficult to express high levels of multiple GPI-anchored CIPs on a single cell in that the biochemical and enzymatic machinery required to form a GPI anchor is limited. This is a further advantage of the invention in cases where the functionality of GPI-anchored CIPs is desired.

In summary, the cCIPs of the present invention provide the advantages that: (1) they act simultaneously as both a C3 and a C5b-9 inhibitor; (2) they require only a single random integration event for expression in transgenic animals thereby significantly increasing the opportunity for the high level expression of two complement inhibitors on a given cell type of the transgenic animal (e.g., endothelial cells); and (3) the expression of a single bifunctional GPI-anchored cCIP is not a burden on the cellular machinery needed to synthesize GPI anchors in those cases where the cCIP is attached to the cell membrane by a GPI anchor.

In connection with this last advantage, higher levels of complement inhibitor activity can be achieved than would be achieved by trying to express two independent GPI-anchored recombinant CIPs in a single cell. This property is a particularly significant advantage in that the degree of complement protection offered to a xenogeneic cell is directly proportional to the number of molecules of complement inhibitor expressed on a cell's surface. See Zhao et al., 1991.

In certain preferred embodiments of the invention, the functional domain having C3 inhibitory activity is DAF or derived from DAF and the functional domain having C5b-9 inhibitory activity is human CD59 or derived from human CD59.

BRIEF DESCRIPTION OF THE DRAWINGS

FIG. 1, panel B is a schematic diagram of the molecular structure of a chimeric molecule having the opposite orientation and designated "CD". The DC molecule exhibits both C3 and C5b-9 inhibitory activity; the CD molecule exhibits only C3 inhibitory activity.

Figure 1A:
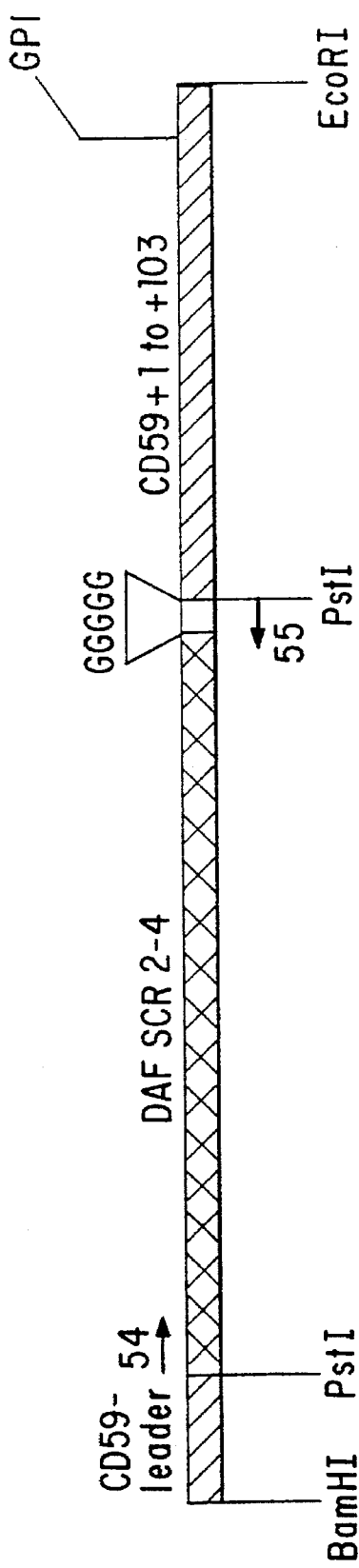
FIG. 1, panel A is a schematic diagram of the molecular structure of a cCIP constructed in accordance with the invention and identified as the "DC" construct. This cCIP has its C3 inhibitory activity amino terminal to its C5b-9 inhibitory activity.

The foregoing drawings, which are incorporated in and constitute part of the specification, illustrate certain aspects of the preferred embodiments of the invention and, together with the description, serve to explain certain principles of the invention. It is to be understood, of course, that both the drawings and the description are explanatory only and are not restrictive of the invention.

DESCRIPTION OF THE PREFERRED EMBODIMENTS

I. The cCIPs of the Invention

As discussed above, the present invention relates to cCIPs which comprise an amino acid sequence having C3 inhibitory activity (hereinafter referred to as a "C3/CIP sequence") and an amino acid sequence having C5b-9 inhibitory activity (hereinafter referred to as a "C5b-9/CIP sequence"), wherein the C3/CIP sequence is amino terminal to the C5b-9/CIP sequence.

The C3/CIP sequence provides the cCIP with C3 inhibitory activity and the C5b-9/CIP sequence provides it with C5b-9 inhibitory activity. The amino acid sequence having C3 inhibitory activity can comprise the entire amino acid sequence for a naturally occurring CIP or a portion thereof, such as one or more SCRs of the CIP.

For example, the C3/CIP sequence can be the mature DAF molecule (i.e., amino acids 1 through 347 of SEQ ID NO:1) or the mature MCP molecule (i.e., amino acids 1 through 350 of SEQ ID NO:3).

Alternatively, the C3/CIP sequence can be a portion of a naturally occurring C3 inhibitor protein. Following the procedures used to identify functional domains of DAF and MCP (Adams, et al., 1991), functional domains of other C3 inhibitors can be identified and used in accordance with the present invention. In general, the portion used should have at least about 25% and preferably at least about 50% of the activity of the parent molecule.

Particularly useful portions of mature C3 inhibitor proteins for use in the present invention comprise one or more of the mature molecule's SCRs. As discussed above, these SCRs are normally approximately 60 amino acids in length and have four conserved cysteine residues which form disulfide bonds, as well as conserved tryptophan, glycine, and phenylalanine/tyrosine residues. In general, more than one SCR is used in the practice of the invention.

As illustrated by the examples presented below, a particularly preferred C3/CIP sequence comprises SCRs 2 through 4 of DAF.

The C5b-9/CIP sequence can comprise the entire amino acid sequence for a naturally occurring C5b-9 inhibitor protein or a portion thereof. For example, the C5b-9/CIP sequence can be the mature CD59 molecule (i.e., amino acids 1 through 103 of SEQ ID NO:2), or a non-human primate C5b-9 inhibitor protein (e.g., amino acids 1 through 103 of SEQ ID NO:4, amino acids 1 through 101 of SEQ ID NO:5, amino acids 1 through 106 of SEQ ID NO:6, amino acids 1 through 103 of SEQ ID NO:7, or amino acids 1 through 103 of SEQ ID NO:8), or a mature HVS-15 inhibitor protein (i.e., amino acids 1 through 102 of SEQ ID NO:9).

Alternatively, the C5b-9/CIP sequence can be a portion of a naturally occurring C5b-9 inhibitor protein. Active portions suitable for use in the present invention can be identified using a variety of assays for C5b-9 inhibitory activity known in the art. See Rollins, et al., 1990; Rollins, et al., 1991; Zhao, et al., 1991; and Rother, et al., 1994. For example, as demonstrated in copending application Ser. No. 08/205,720, entitled "Terminal Complement Inhibitor Fusion Genes and Proteins," which is referred to above, the relevant portions of which are incorporated herein by reference, amino acids 1 through 77 of CD59 comprise a portion of the CD59 molecule having C5b-9 inhibitory activity. In general, the portion used should have at least about 25% and preferably at least about 50% of the activity of the parent molecule.

As discussed above, naturally occurring C5b-9 inhibitor proteins generally share a common motif which can be described by formulas (1) or (2) above. Preferred portions of mature C5b-9 inhibitor proteins for use with the present invention are those having the amino acid sequence defined by these formulas. Petranka et al., 1993, and Norris et al., 1993, have reported that in CD59 (SEQ ID NO:2), the disulfide bond between Cys6 and Cys13, as well as the disulfide bond between Cys64 and Cys69, can be disrupted by replacement of these cysteines with serines without substantially compromising the functionality of CD59. These cysteines correspond to the second, third, ninth, and tenth cysteines in the above formulas. Accordingly, portions of mature C5b-9 inhibitor proteins having the above formulas but with all or some of the above cysteines replaced with serine, or another amino acid, can be used in the practice of the invention.

As discussed above, the critical aspect of the invention is the order in which the amino acid sequence having C3 inhibitory activity and the amino acid sequence having C5b-9 inhibitory activity appear in the chimeric molecule. As demonstrated by the examples presented below, the amino acid sequence having C3 inhibitory activity must be amino terminal to the amino acid sequence having C5b-9 inhibitory activity. The opposite order only produces C3 inhibitory activity.

The amino acid sequence having C3 inhibitory activity and the amino acid sequence having C5b-9 inhibitory activity do not have to be directly attached to one another. Rather, a linker sequence can separate these two sequences. The linker preferably comprises between one and about ten amino acids, although more amino acids can be used if desired. In the examples presented below, glycines were used to form the linker. This amino acid has been found to perform successfully in other chimeric proteins which include linker regions. See Curtis, et al., "Fusion Proteins Comprising GM-CSF and IL-3" U.S. Pat. No. 5,073,627. Other amino acids, as well as combinations of amino acids, can be used in the linker region if desired.

In the examples presented below, the amino acid sequence having C5b-9 inhibitory activity includes a GPI-anchor which attaches the chimeric CIP to the cell membrane. CIPs having C5b-9 inhibitory activity and attached to the cell membrane by a transmembrane domain, rather than a GPI-anchor, are described in copending application Ser. No. 08/205,720, entitled "Terminal Complement Inhibitor Fusion Genes and Proteins," which is referred to above, the relevant portions of which are incorporated herein by reference. Such transmembrane domains for cell membrane attachment can be used in the practice of the present invention.

As discussed above, the cCIPs of the invention through the ordering of the C3/CIP sequence and the C5b-9/CIP sequence exhibit both C3 inhibitory activity and C5b-9 inhibitory activity. The chimeric molecules exhibit at least about 25% and preferably at least about 50% of the inhibitory activity of the parent inhibitor protein from which the chimera is constructed. In this way, the advantages of providing both types of complement inhibition in one molecule, as discussed above, are achieved.

II. cCIP Genes and Vectors Containing Such Genes

Molecules comprising nucleotide sequences encoding the cCIPs of the invention can be prepared using a variety of techniques now known or subsequently developed in the art. For example, the cCIPs can be produced using PCR generation and/or restriction digestion of cloned genes to generate fragments encoding amino acid sequences having C3 and C5b-9 inhibitory activities. These fragments can be assembled using PCR fusion or enzymatic ligation of the restriction digestion products (Sambrook, et al., 1989; Ausubel et al., 1992). Alternatively, the nucleic acid molecules encoding the cCIPs of the invention or any or all of the nucleic acid fragments used to assemble the chimeric genes for the cCIPs can be synthesized by chemical means (Talib, et al., 1991).

The nucleic acid molecules which encode the cCIPs of the invention can contain additional sequences to those which encode the amino acid sequences which impart C3 and C5b-9 inhibitory activity to the molecule. For example, as discussed above, the chimeric protein can include a linker sequence, in which case the nucleic acid molecule will contain a corresponding sequence which codes for the linker. In addition, to allow for processing by host cells, the nucleic acid sequence will preferably encode a signal peptide at its 5' end which directs the transport of the chimeric protein to the exterior of the cell. A suitable leader sequence is one naturally associated with a CIP, such as, the leader sequence for CD59, i.e., amino acids −25 through −1 of SEQ ID NO:2.

In cases where only a portion of a full length CIP having the desired inhibitory activity is included in the chimeric molecule, the cloning procedure can begin with the nucleic acid sequence for the full CIP molecule. The desired portion of the nucleic acid molecule can then be obtained from the full molecule using PCR or restriction digestion techniques.

In addition to the foregoing, the present invention provides recombinant expression vectors which include nucleic acid fragments encoding the cCIPs of the invention. The nucleic acid molecule coding for such a chimeric protein can be inserted into an appropriate expression vector, i.e., a vector that contains the necessary elements for the transcription and translation of the inserted protein-encoding sequence. The necessary transcriptional and translational signals can also be supplied by the genes used to construct the fusion genes of the invention and/or their flanking regions.

The transcriptional and translational control sequences for expression vector systems to be used to direct expression in vertebrate cells may be provided by viral sources. For example, commonly used promoters and enhancers are derived from Polyoma virus, Adenovirus, Simian Virus 40 (SV40), the Molony murine leukemia virus (MMLV), including the long terminal repeat (MMLV-LTR), and human cytomegalovirus (CMV), including the cytomegalovirus immediate-early gene 1 promoter and enhancer. Retroviral expression vectors are a preferred system for expression of the cCIPs of the invention.

The manipulation of retroviral nucleic acids to construct retroviral vectors and packaging cells is accomplished using techniques known in the art. See Ausubel, et al., 1992, Volume 1, Section III (units 9.10.1–9.14.3); Sambrook, et al., 1989; Miller, et al., 1989; Eglitis, et al., 1988; U.S. Pat. Nos. 4,650,764, 4,861,719, 4,980,289, 5,122,767, and 5,124,263; as well as PCT Patent Publications Nos. WO 85/05629, WO 89/07150, WO 90/02797, WO 90/02806, WO 90/13641, WO 92/05266, WO 92/07943, WO 92/14829, and WO 93/14188.

In particular, the retroviral vectors of the invention can be prepared and used as follows. First, a CCIP retroviral vector is constructed and packaged into non-infectious transducing viral particles (virions) using an amphotropic packaging system, preferably one suitable for use in gene therapy applications.

Examples of such packaging systems are found in, for example, Miller, et al., 1986; Markowitz, et al., 1988; Cosset, et al., 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. A preferred packaging cell is the PA317 packaging cell line (ATCC CRL 9078).

The generation of "producer cells" is accomplished by introducing retroviral vectors into the packaging cells. Examples of such retroviral vectors are found in, for example, Korman, et al., 1987; Morgenstern, et al., 1990; U.S. Pat. Nos. 4,405,712, 4,980,289, and 5,112,767; and PCT Patent Publications Nos. WO 85/05629, WO 90/02797, and WO 92/07943. A preferred retrovital vector is the MMLV derived expression vector pLXSN (Miller, et al., 1989). The retroviral vector used in the practice of the present invention will be modified to include the chimeric gene encoding the cCIP.

The producer cells generated by the foregoing procedures are used to produce the retroviral vector particles (virions). This is accomplished by culturing of the cells in a suitable growth medium. Preferably, the virions are harvested from the culture and administered to the target cells which are to be transduced, e.g., xenogeneic cells to be used for transplantation into a patient whose complement can be inhibited by the cCIP, cells of a xenogeneic organ to be used for transplantation into such a patient, the patient's own cells, and other cells to be protected from complement attack, as well as stem cells such as embryonic stem cells, which can be used to generate transgenic cells, tissues, or organs for transplantation. Alternatively, when practicable, the target cells can be co-cultured with the producer cells. Suitable buffers and conditions for stable storage and subsequent use of the virions can be found in, for example, Ausubel, et al., 1992.

Pharmaceutical compositions containing the retroviral vector particles of the invention can be administered in a variety of unit dosage forms. The dose will vary according to, e.g., the particular vector, the manner of administration, the particular disease being treated and its severity, the overall health and condition and age of the patient, the condition of the cells being treated, and the judgment of the physician. Dosage levels for transduction of mammalian cells are generally between about $10^6$ and $10^{14}$ colony forming units of retroviral vector particles per treatment.

A variety of pharmaceutical formulations can be used for administration of the retroviral vector particles of the invention. Suitable formulations are found in, for example, *Remington's Pharmaceutical Sciences*, Mack Publishing Company, Philadelphia, Pa., 17th ed., 1985, and will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

III. Transgenic Animals

In accordance with certain aspects of the invention, the nucleic acid molecules of the present invention are used to generate engineered transgenic animals (for example, rodent, e.g., mouse, rat, capybara, and the like, lagomorph, e.g., rabbit, hare, and the like, ungulate, e.g., pig, cow, goat, sheep, and the like, etc.) that express the cCIPs of the invention on the surfaces of their cells (e.g., endothelial cells) using techniques known in the art. These techniques include, but are not limited to, microinjection, e.g., of pronuclei, electroporation of ova or zygotes, nuclear transplantation, and/or the stable transfection or transduction of embryonic stem cells derived from the animal of choice.

A common element of these techniques involves the preparation of a transgene transcription unit. Such a unit comprises a DNA molecule which generally includes: 1) a promoter, 2) the nucleic acid sequence of interest, i.e., the sequence encoding the cCIP of the present invention, and 3)

a polyadenylation signal sequence. Other sequences, such as, enhancer and intron sequences, can be included if desired. The unit can be conveniently prepared by isolating a restriction fragment of a plasmid vector which expresses the cCIP protein in, for example, mammalian cells. Preferably, the restriction fragment is free of sequences which direct replication in bacterial host cells since such sequences are known to have deleterious effects on embryo viability.

The most well known method for making transgenic animals is that used to produce transgenic mice by superovulation of a donor female, surgical removal of the egg, injection of the transgene transcription unit into the pronuclei of the embryo, and introduction of the transgenic embryo into the reproductive tract of a pseudopregnant host mother, usually of the same species. See Wagner, U.S. Pat. No. 4,873,191, Brinster, et al., 1985, Hogan, et al., 1986, Robertson 1987, Pedersen, et al., 1990.

The use of this method to make transgenic livestock is also widely practiced by those of skill in the art. As an example, transgenic swine are routinely produced by the microinjection of a transgene transcription unit into pig embryos. See, for example, PCT Publication No. WO92/11757. In brief, this procedure may, for example, be performed as follows.

First, the transgene transcription unit is gel isolated and extensively purified through, for example, an ELUTIP column (Schleicher & Schuell, Keene, N.H.), dialyzed against pyrogen free injection buffer (10 mM Tris, pH 7.4+0.1 mM EDTA in pyrogen free water) and used for embryo injection.

Embryos are recovered from the oviduct of a hormonally synchronized, ovulation induced sow, preferably at the pronuclear stage. They are placed into a 1.5 ml microfuge tube containing approximately 0.5 ml of embryo transfer media (phosphate buffered saline with 10% fetal calf serum). These are centrifuged for 12 minutes at 16,000×g in a microcentrifuge. Embryos are removed from the microfuge tube with a drawn and polished Pasteur pipette and placed into a 35 mm petri dish for examination. If the cytoplasm is still opaque with lipid such that the pronuclei are not clearly visible, the embryos are centrifuged again for an additional 15 minutes. Embryos to be microinjected are placed into a drop of media (approximately 100 μl) in the center of the lid of a 100 mm petri dish. Silicone oil is used to cover this drop and to fill the lid to prevent the medium from evaporating. The petri dish lid containing the embryos is set onto an inverted microscope equipped with both a heated stage (37.5°–38° C.) and Hoffman modulation contrast optics (200× final magnification). A finely drawn and polished micropipette is used to stabilize the embryos while about 1–2 picoliters of injection buffer containing approximately 200–500 copies of the purified transgene transcription unit is delivered into the nucleus, preferably the male pronucleus, with another finely drawn and polished micropipette. Embryos surviving the microinjection process as judged by morphological observation are loaded into a polypropylene tube (2 mm ID) for transfer into the recipient pseudopregnant sow.

Offspring are tested for the presence of the transgene by isolating genomic DNA from tissue removed from the tail of each piglet and subjecting about 5 micrograms of this genomic DNA to nucleic acid hybridization analysis with a transgene specific probe.

Another commonly used technique for generating transgenic animals involves the genetic manipulation of embryonic stem cells (ES cells) as described in PCT Patent Publication No. WO 93/02188 and Robertson, 1987. In accordance with this technique, ES cells are grown as described in, for example, Robertson, 1987, and in U.S. Pat. No. 5,166,065 to Williams et al. Genetic material is introduced into the embryonic stem cells by, for example, electroporation according, for example, to the method of McMahon, et al., 1990, or by transduction with a retroviral vector according, for example, to the method of Robertson, et al., 1986, or by any of the various techniques described by Lovell-Badge, 1987.

Chimeric animals are generated as described, for example, in Bradley, 1987. Briefly, genetically modified ES cells are introduced into blastocysts and the modified blastocysts are then implanted in pseudo-pregnant female animals. Chimeras are selected from the offspring, for example by the observation of mosaic coat coloration resulting from differences in the strain used to prepare the ES cells and the strain used to prepare the blastocysts, and are bred to produce non-chimeric transgenic animals.

Other methods for the production of transgenic animals are disclosed in U.S. Pat. No. 5,032,407 to Wagner et al., and PCT Publication No. WO90/08832.

Among other applications, transgenic animals prepared in accordance with the invention are useful as model systems for testing the xenotransplantation of their engineered tissues or organs and as sources of engineered tissues or organs for xenotransplantation. The expression of functional cCIPs on the surfaces of endothelial cells and/or other cell types in the tissues and organs (e.g., hormone producing cells such as those in the pancreatic islets) of the transgenic animals will provide enhanced protection to those cells, tissues and organs from hyperacute complement-mediated rejection following xenotransplantation in recipient animals, e.g., humans, whose complement can be inhibited by the cCIP. In addition to their use in producing organs for transplantation, the cCIP nucleic acid constructs of the invention can also be used to engineer cultured cells (e.g., endothelial cells) of various species for subsequent use in transplantation.

IV. Representative Modifications

Although specific embodiments of the invention are described and illustrated herein, it is to be understood that modifications can be made without departing from the invention's spirit and scope.

For example, the primary amino acid structures of the cCIPs of the invention may be modified by creating amino acid substitutions or nucleic acid mutations. At least some complement regulatory activity should remain after such modifications. Similarly, nucleic acid mutations which do not change the amino acid sequences, e.g., third nucleotide changes in degenerate codons, are included within the scope of the invention. Also included are sequences comprising changes that are found as naturally occurring allelic variants of the genes for the C3/CIPs and the C5b-9/CIPs used to create the cCIPs.

Without intending to limit it in any manner, the present invention will be more fully described by the following examples.

EXAMPLE 1

Construction of a Polynucleotide Encoding DC

Figure 1B:
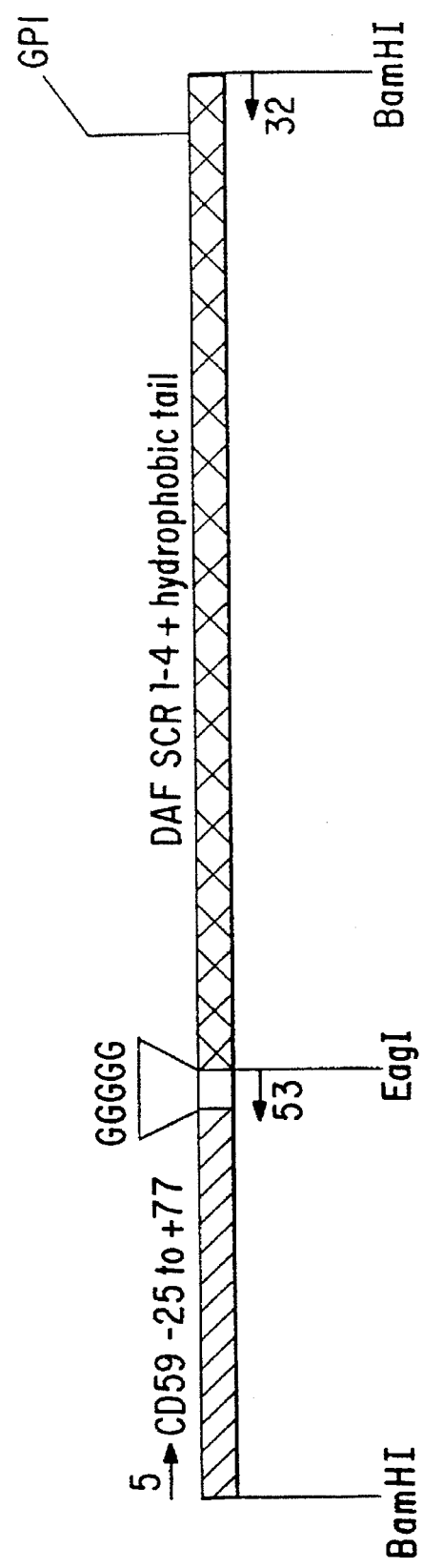
Figure 2B:
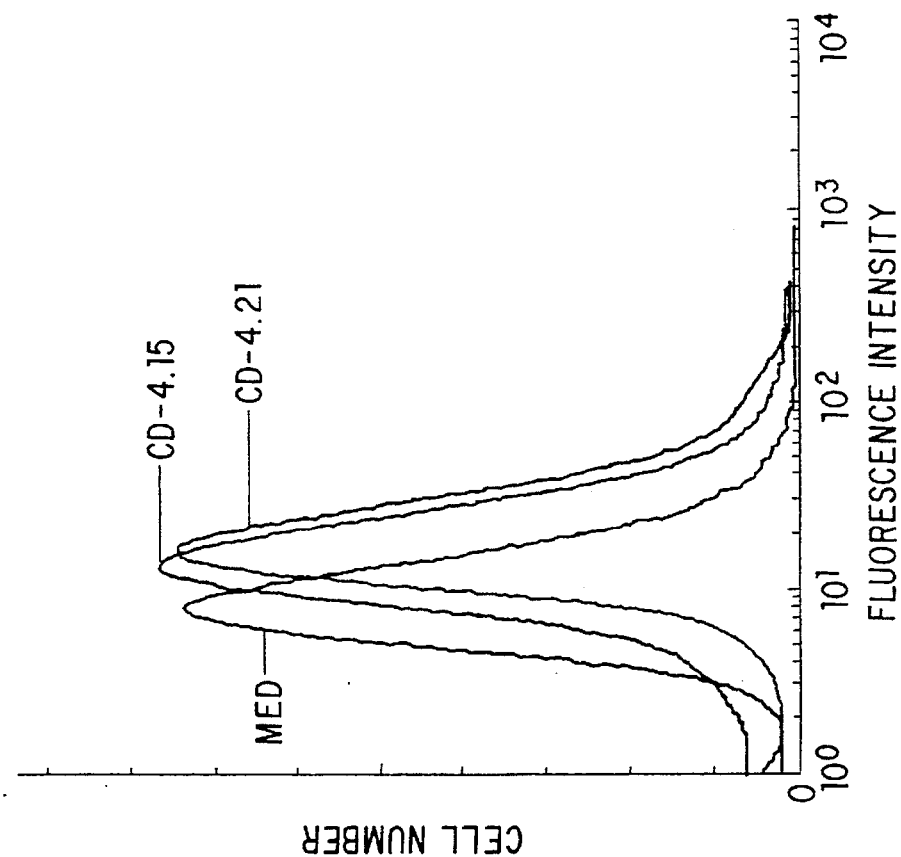
FIG. 2 shows the results of flow cytometric analysis of the cell surface expression of the DC and CD molecules.
Figure 2A:
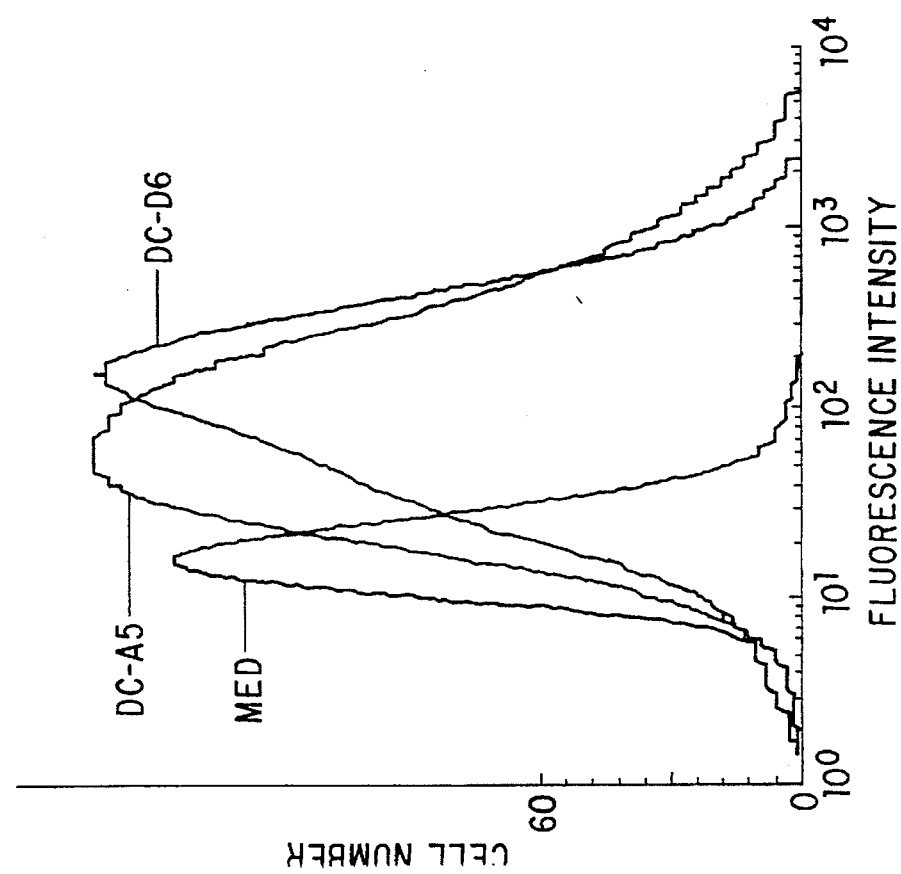
Figure 2D:
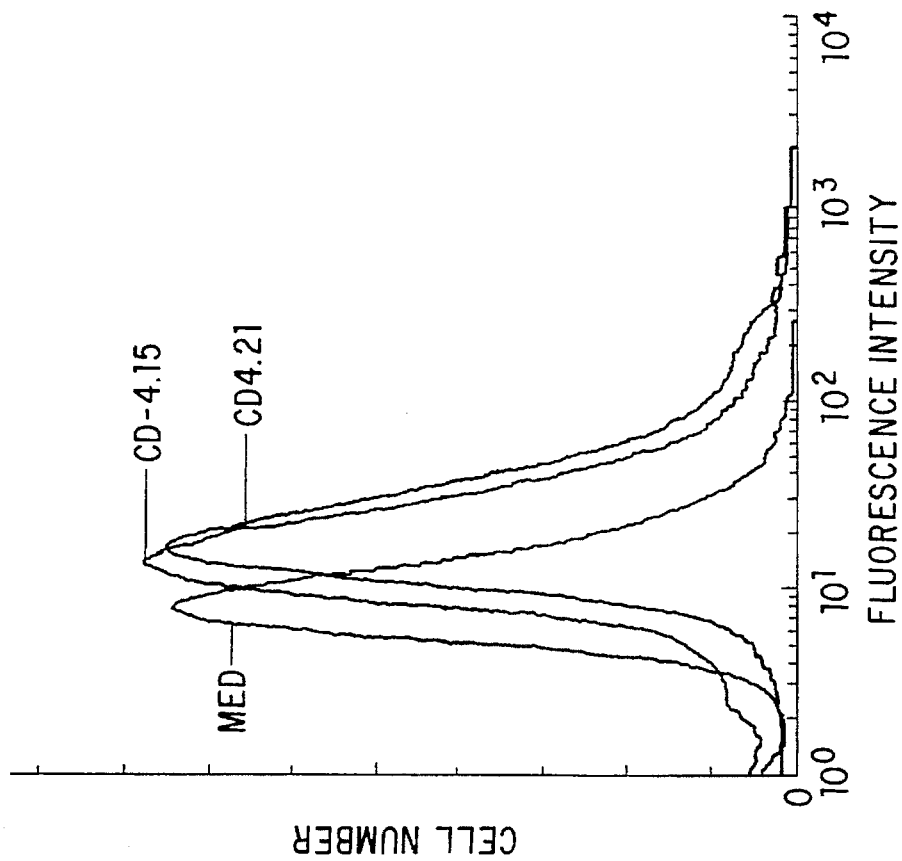
Figure 2C:
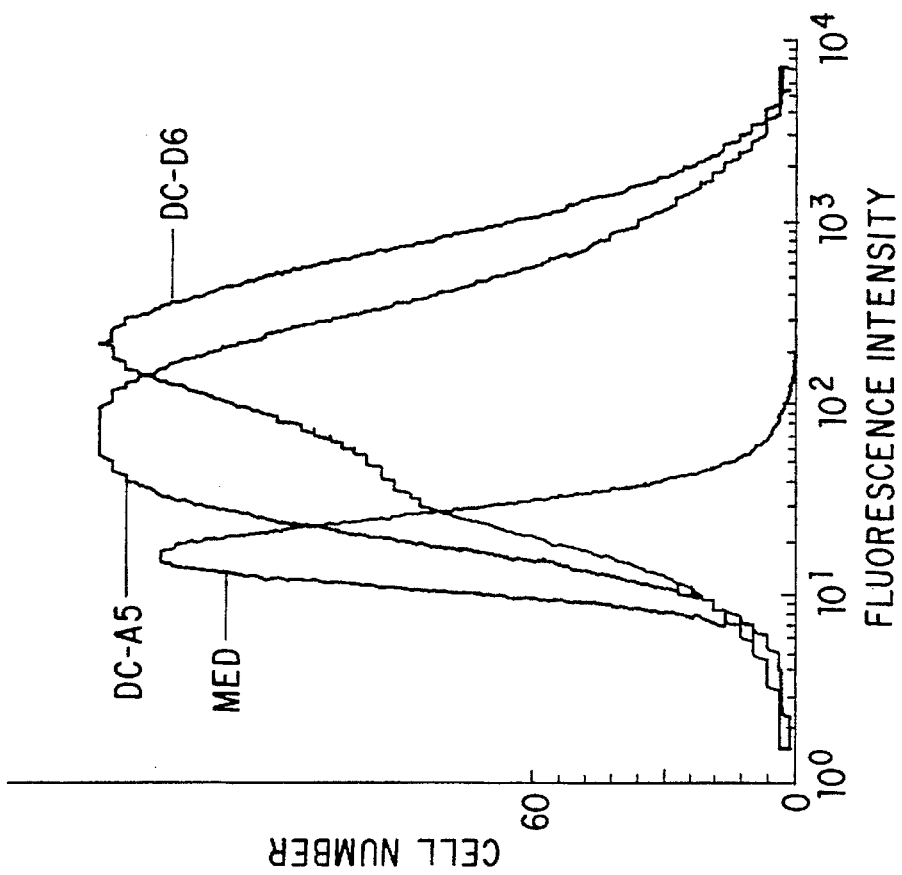

The cCIP designated DC is a chimeric combination of the amino terminal leader peptide sequence of the immature CD59 polypeptide, a fragment of the DAF polypeptide containing the second, third, and fourth SCRs, a linker region comprising five Gly residues, and a peptide containing residues 1 to 103 of the mature CD59 polypeptide (FIG. 1, panel A). The leader peptide is normally removed from the nascent CD59 polypeptide after directing its transport to the exterior of the cell. Also, at least some of the carboxyl terminal amino acids of the CD59 polypeptide are removed during attachment of the GPI anchor that tethers the cCIP to the cell membrane.

DC includes, in order, amino acids −25 to +2 of SEQ ID NO:2, amino acids 62 to 251 of SEQ ID NO:1, four additional glycine residues, and amino acids 1 to 103 of SEQ ID NO:2.

The chimeric DNA construct encoding DC was prepared by first preparing a PCR-generated DNA fragment flanked with PstI sites and digested with PstI. This PstI digested PCR generated fragment (referred to hereinafter as the PstI flanked fragment) contains sequences encoding a glycine bridge as well as a fragment of DAF spanning amino acid 62 to amino acid 251 of SEQ ID NO:1. The PstI flanked fragment was ligated into the unique PstI site at the junction between the leader peptide and mature protein-encoding regions of a full length CD59 clone in plasmid pGEM7Zf (Promega Corporation, Madison, Wis.) containing the same CD59 encoding insert as plasmid pC8-hCD59-103, (ATCC designation 69231).

The template for the PCR reaction used to produce the PstI flanked fragment was a SalI-BamHI flanked truncated DAF cDNA clone containing sequences of DAF encoding amino acids −34 to 337 of SEQ ID NO:1, ending 10 amino acids short of the carboxyl-terminus of the full length DAF polypeptide. This SalI-BamHI flanked clone was prepared by PCR using HeLa cell (human) first strand cDNA as template. Cytoplasmic RNA was prepared from approximately $5 \times 10^6$ cells, and first strand cDNA was synthesized from 4 μg of RNA in a final volume of 100 μl using the following reaction conditions: 10 mM Tris-HCl pH 8.3; 50 mM KCl; 1.5 mM $MgCl_2$; 800 ng oligo(dT)$_{15}$ (Promega Corporation, Madison, Wis.); 10 mM DTT; 0.25 mM dNTPs (dG, dC, dA, dT); 40 U RNasin (Promega Corporation, Madison, Wis.); and 20 U Avian Myeloblastosis Virus reverse transcriptase (Seikagaku of America, Inc. Rockville, Md.) at 42° C. for one hour.

PCR was performed following cDNA synthesis using 8 μl of first strand cDNA reaction mixture as template and the following primers: 5' primer (oligo A; SEQ ID NO:10)—5' CGCTGGGCGT AGCGTCGACT CGGCGGAGTC CCG 3'; and 3' primer (oligo B; SEQ ID NO:11)—5' GCCCATG-GAT CCTAGCGTCT AAAGCAAACC TGTCAACG 3'. The PCR reaction mixture (final volume 100 μl) contained the following reaction components: 10 mM Tris-HCl pH 8.3; 50 mM KCl; 3.5 mM $MgCl_2$; 1.6 mM dNTPs; 100 ng oligo A; 100 ng oligo B; and 5 U AmpliTaq (Perkin-Elmer Corporation, Norwalk, Conn.). The PCR conditions were 95° C. 1 minute, 59° C. 1 minute, 72° C. 3 minutes for a total of 35 cycles, followed by a 10 minute extension at 72° C.

This PCR reaction produced a single DNA fragment of approximately 1200 nucleotides that was TA subcloned as an insert into plasmid pCRII according to the manufacturers directions (Invitrogen, San Diego, Calif.), yielding plasmid pDAF-#10. A BamHI fragment of pDAF-#10 containing the PCR generated sequences was subcloned into plasmid pcDNAI/AMP (Invitrogen, San Diego, Calif.) and clones were analyzed by sequencing to identify a clone with the insert in the correct orientation for expression, plasmid pDAF-c#18. The nucleotide sequence of the insert was confirmed by sequence analysis to include the sequence spanning nucleotides 78 to 1166 of SEQ ID NO:1.

PCR to produce the PstI flanked fragment was carried out using essentially the same conditions as recited above, except that the template was approximately 50 ng of BamH1 linearized plasmid pDAF-c#18, the primers were oligo 54 (5' primer—5' GAAGAGTTCT GCAGAATCGT AGCT-GCGAGG TGCC 3'; SEQ ID NO:12) and oligo 55 (3' primer—5' CCACGTGCTG CAGTCCTCCA CCTCCTC-CTC TGCATTCAGG TGGTGGG 3'; SEQ ID NO:13), and the PCR conditions were: an initial denaturation step of 95° C. 3 minutes, followed by 20 cycles of 95° C. 1 minute, 55° C. 1 minute, 72° C. 1 minute, followed by a 10 minute extension at 72° C.. The PCR product of this reaction electrophoresed as a band of approximately 500 to 600 nucleotides in length. This PCR generated fragment was TA subcloned as an insert into plasmid pCRII (Invitrogen, San Diego, Calif.), and sequenced to confirm that the insert contained the sequence spanning nucleotides 339 to 908 of SEQ ID NO:1. The pCRII clone was cut with PstI to yield the PstI flanked fragment, which was ligated into the unique PstI site (spanning nucleotides 138 to 143 of SEQ ID NO:2) in the insert in the full length CD59 clone in plasmid pGEM7Zf (referred to above). The pGEM7Zf vector sequences were separated from the resulting chimeric insert with BamHI and EcoRI, and the resulting chimetic BamHI-EcoRI fragment was subcloned into BamHI EcoRI cut pcDNAI/AMP (Invitrogen, San Diego, Calif.) to yield plasmid pDCN#1-pcDNAI-AMP (ATCC designation 69563) referred to hereinafter as construct DC.

EXAMPLE 2

Construction of Polynucleotides Encoding CD and Full Length DAF

Vectors were constructed directing the expression of full length DAF as well as of molecules with CD59 sequences located amino-terminal to DAF sequences, i.e., CD molecules. The pDAF-c#18 vector described in Example 1 was re-engineered in several steps to encode the full carboxyl-terminal region of DAF and a complete DAF amino terminal leader peptide.

Vectors directing the synthesis of a CD molecule were prepared comprising the carboxyl-terminal truncated form of DAF and were subsequently re-engineered in the same fashion as was pDAF-c#18 to encode the full carboxyl-terminal region of DAF.

The pDAF-c#18 vector was re-engineered to encode a complete DAF amino terminal leader peptide after sequence analysis revealed that the PCR reaction had generated a mutant leader sequence. The correct leader sequence was provided by a pair of complementary oligonucleotides, oligo 173 (5' TGCACGGATC CATGACCGTC GCGCGGCCGA GCGTGCCCGC 3'; SEQ ID NO:18) and oligo 174 (5' GGGCACGCTC GGCCGCGCGA CGGTCATGGA TCCG 3'; SEQ ID NO:19) that contained the correct sequence of the DAF leader. These oligos were designed to have, upon annealing to each other, restriction site overhangs complementary to the engineered SalI site introduced by oligo A, and the SacII site spanning nucleotides 78–84 of SEQ ID NO:1.

Oligo 173 and 174 were kinased, annealed, and ligated into pDAF-c#18 after digestion of the plasmid with SalI and SacII to remove the defective leader peptide region. The integrity of the leader coding region of the resulting construct, plasmid pDAF-L, was confirmed by sequence analysis.

An expression vector directing the expression of a CD molecule containing the carboxyl-terminal truncated DAF domain was constructed using a BamHI-EagI fragment obtained from the pDAF-c#18 plasmid and a CD59 cDNA BamHI-EagI fragment that was generated by PCR and restriction enzyme digestion. The PCR reaction was carried out using oligo 5 (5' primer—5' GGAAGAGGAT CCTGGGCGCC GCAGG 3'; SEQ ID NO:14) and oligo 53 (3' primer—5' GGTCTTCGGC CGCTCCACCT CCCCCACCAT TTTCAAGCTG TTCG 3'; SEQ ID NO:15) using a full length CD59 cDNA BamHi-EcoRI fragment as template.

Conditions for this reaction were essentially as described for the PCR reactions of Example 1, except that the program was an initial denaturation step of 95° C. 3 minutes, followed by 10 cycles of 95° C. 1 minute, 52° C. 1 minute, 72° C. 1 minute, followed by 10 cycles of 95° C. 1 minute, 58° C. 1 minute, 72° C. 1 minute, followed by a 10 minute extension at 72° C. Oligo 53 contains sequences that encode glycine residues of the glycine linker and an EagI restriction site for cloning. Oligo 5 comprises a BamHI site approximately 30 base pairs upstream (5') to amino acid −25 of CD59 (SEQ ID NO:2).

The approximately 330 base pair PCR product was TA subcloned as an insert into plasmid pCRII (Invitrogen, San Diego, Calif.), and sequenced to confirm that the insert contained the sequence spanning nucleotides 27 to 374 of SEQ ID NO:2. This pCRII subclone was digested with BamHI and EagI. The two fragments, i.e., the DAF BamHI-EagI fragment and the CD59 BamHI EagI fragment, were ligated in a three-way ligation into BamHI digested vector pcDNAI/Amp (Invitrogen, San Diego, Calif.) and restriction mapping was undertaken to identify a clone with the correct fragment order for expression, plasmid pCD-pcDNAI-AMP.

Plasmid pCD-pcDNAI-AMP was tested and found not to direct detectable expression of DAF immunoreactive material on mammalian cells. This lack of expression was attributed to the carboxyl-terminal truncations present in the DAF-encoding regions in this vector. This vector and the pDAF-L vector were therefore re-engineered to encode the full carboxyl-terminal region of DAF by PCR addition of a synthetic polynucleotide carboxyl-terminus as follows.

Oligo 175 (5' primer—5' CCCCAAATAA AGGAAGTGGA ACCACTTCAG GTACTACCC 3'; SEQ ID NO:16) and oligo 176 (3' primer—5' GGCTAAGTCA GCAAGCCCAT GGTTACTAGC GTCCCAAGCA AACC 3'; SEQ ID NO:17) were used to add the final ten carboxyl terminal amino acids of DAF to plasmids pDAF-L and pCD-pcDNAI-AMP. Oligo 175 spans an XmnI site present in the DAF sequence, and oligo 176 contains an EcoRI site.

Conditions for this reaction were essentially as described for the PCR reactions of Example 1, except that the template was approximately 13 ng of pDAF-c#18 and the program was 5 cycles of 95° C. 1 minute, 50° C. 1 minute, 72° C. 1 minute with only oligo 176 present in the reaction mixture, followed by addition of oligo 175 and 20 cycles of 95° C. 1 minute, 58° C. 1 minute, 72° C. 1 minute, followed by a 10 minute extension at 72° C.

The approximately 120 base pair PCR product was TA subcloned as an insert fragment into plasmid pCRII (Invitrogen, San Diego, Calif.), and sequenced to confirm that the insert contained the sequence spanning nucleotides 1184 to 1196 of SEQ ID NO:1. An EcoRI-XmnI fragment isolated from this pCRII subclone was used to replace the partially homologous BamHI-XmnI fragments of plasmids pDAF-L and pCD-pcDNAI-AMP. The resulting plasmids were pFLDAF (referred to hereinafter as construct DAF) and pCDGPI#1-pcDNAI-AMP (ATCC designation 69564; referred to hereinafter as construct CD).

Construct CD comprises sequences encoding residues −25 to +79 of SEQ ID NO:2 (CD59—negatively numbered residues being part of the leader peptide sequence described above), a glycine linker region including five glycine residues, two of which are amino acids 78 and 79 of SEQ ID NO:2 and three of which were engineered into the PCR primer used to generate the CD59-encoding DNA fragment, and a fragment of the DAF polypeptide including SCRs 1–4 together with the contiguous hydrophobic tail sequence of DAF (FIG. 1, panel B).

This DAF-encoding region starts at an EagI site 5 amino acids N-terminal to SCR1, i.e., it starts at amino acid −5 of SEQ ID NO:1, and ends at amino acid 347 of SEQ ID NO:1, so that it encodes the complete C-terminus of DAF. The carboxyl-terminal portion of this region includes nucleotides encoding the putative GPI anchoring signal sequence of DAF.

EXAMPLE 3

Cell Surface Expression of DC and CD in Mammalian Cells

Stable transfection of constructs DAF, DC and CD was performed into the murine fibroblast cell line, Balb/3T3, by calcium phosphate transfection (Ausubel, et al., 1992). Co-transfection of the plasmid SV2Neo permitted selection on G418 (Gibco) containing media. G418 resistant colonies were then picked, expanded, and tested for the presence of cell surface expressed DC and CD by indirect immunofluorescence, using the anti-DAF monoclonal antibody BRIC 216 (Serotec, Indianapolis, Ind.) and the anti-CD59 monoclonal antibody MEM43 (Biodesign International, Kennebunkport, Me.) and anti-murine secondary (2°) antibodies conjugated to FITC. Increased fluorescence relates to increased cell surface expression. FIG. 2 illustrates cell surface expression profiles of two independent positive clones of DC (DC-A5 and DC-D6; FIG. 2, panels A and C) as well as two independent CD clones (CD-4.15 and CD-4.21; FIG. 2, panels B and D) relative to cells transfected with SV2Neo alone as a negative control.

The flow cytometric profiles shown in FIG. 2 illustrate that DC and CD are each expressed on the surface of the stably transfected Balb/3T3 cells and are recognized by both anti-DAF and anti-CD59 monoclonal antibodies. These results indicate that these molecules retain at least some of the conformational epitopes inherent in the native parental inhibitors DAF and CD59.

EXAMPLE 4

PI-PLC Analysis of DC Expressed in Mammalian Cells

A structural feature of CD59 is the anchoring of the protein to the cell surface membrane through a glycosyl-phosphatidylinositol (GPI) linkage. As discussed above, DC contains the entire CD59 amino acid sequence fused with a large portion of the DAF polypeptide. To test whether this chimeric molecule is also retained on the cell surface via a GPI linkage, PI-PLC (Boehringer-Mannheim, Corporation, Biomedical Products Division, Indianapolis, Ind.) digestion was performed on Balb/3T3 cells expressing DC at 1 U/ml for 1 hr at 37° C. prior to FACS analysis. The result of that experiment is presented in FIG. 3.

Figure 3A:
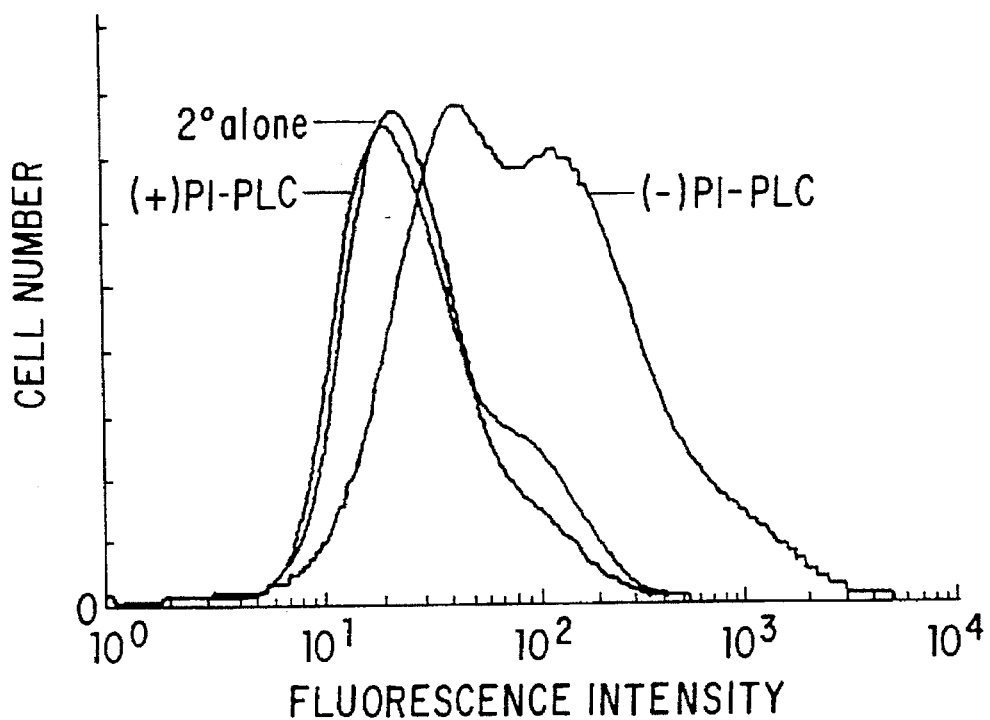
FIG. 3 shows the results of flow cytometric analysis of the cell surface expression of the DC cCIP before and after treatment with PI-PLC.
Figure 3B:
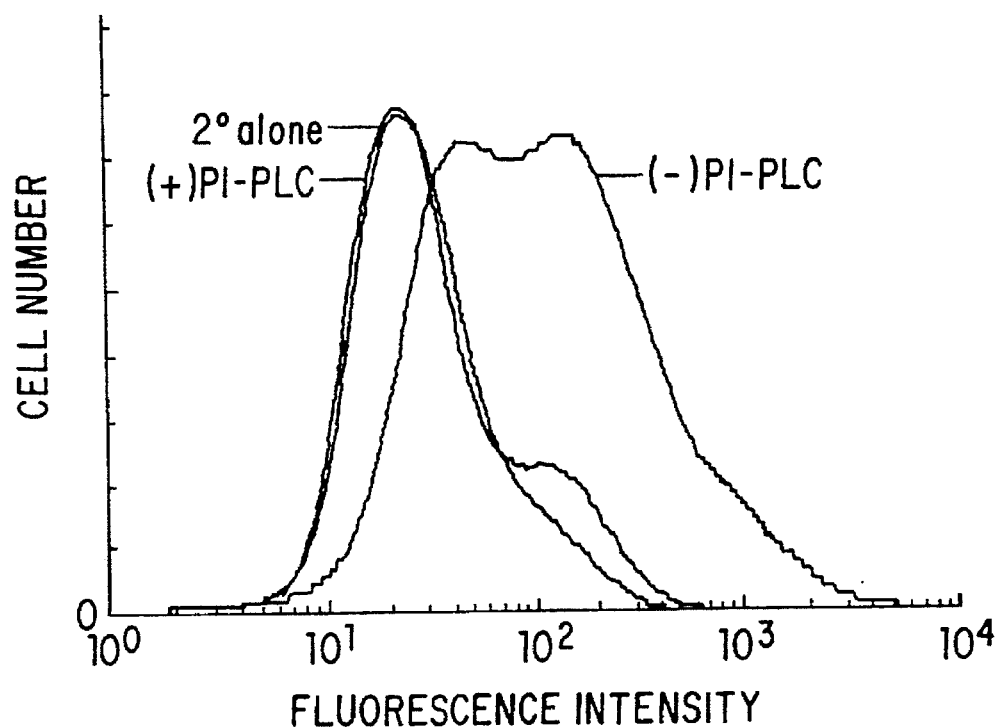
Figure 4A:
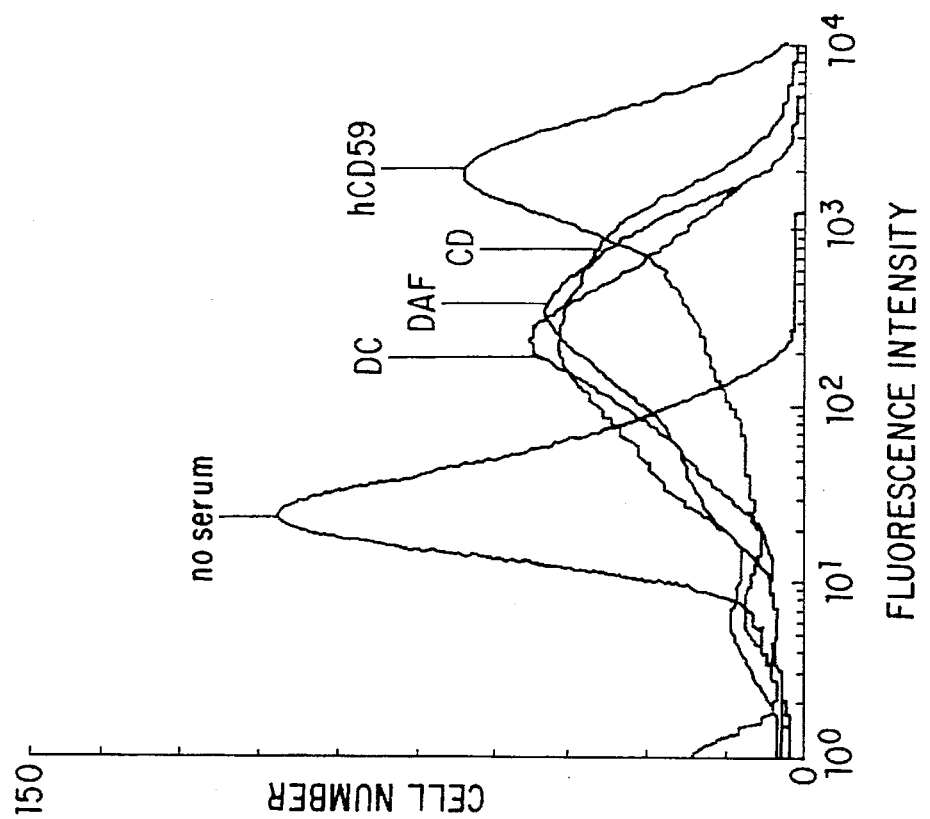
FIG. 4 shows the results of flow cytometric analysis of the degree of C3 deposition on the surface of mammalian cells expressing the DC cCIP following incubation with increasing concentrations of whole human serum. Cell surface C3 deposition (usually in the form of proteolytic fragments of C3) is a measure of C3 convertase activity. In this figure, the degree of C3 convertase inhibition provided by DC is compared with that provided by CD, DAF, and CD59.
Figure 4B:
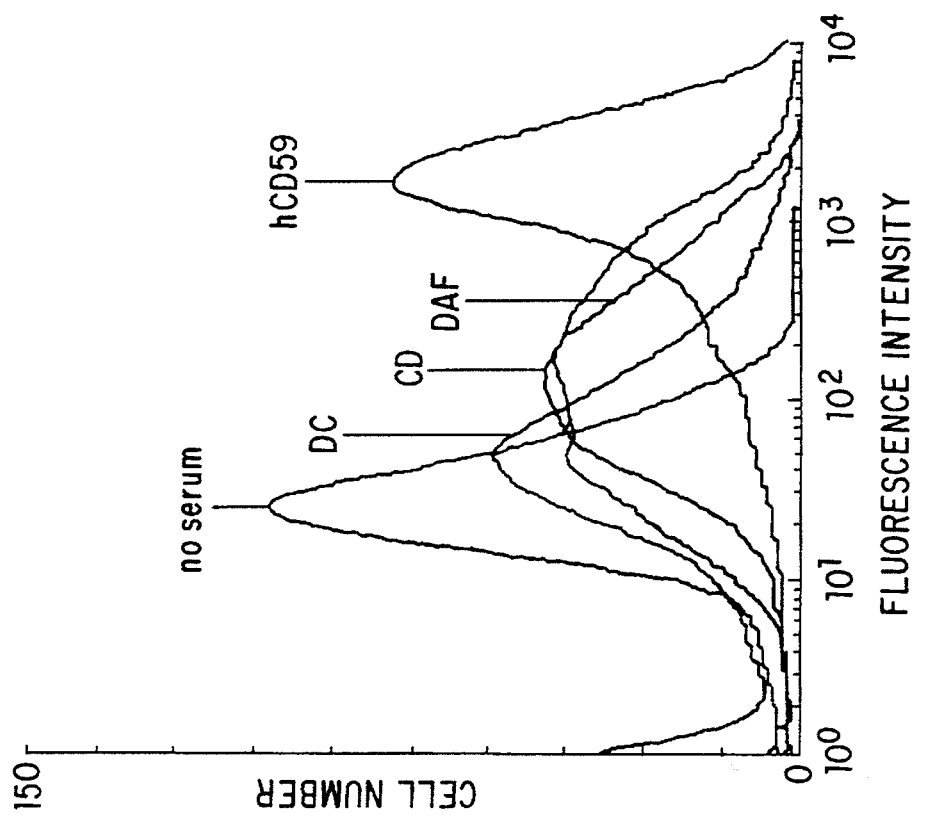
Figure 4D:
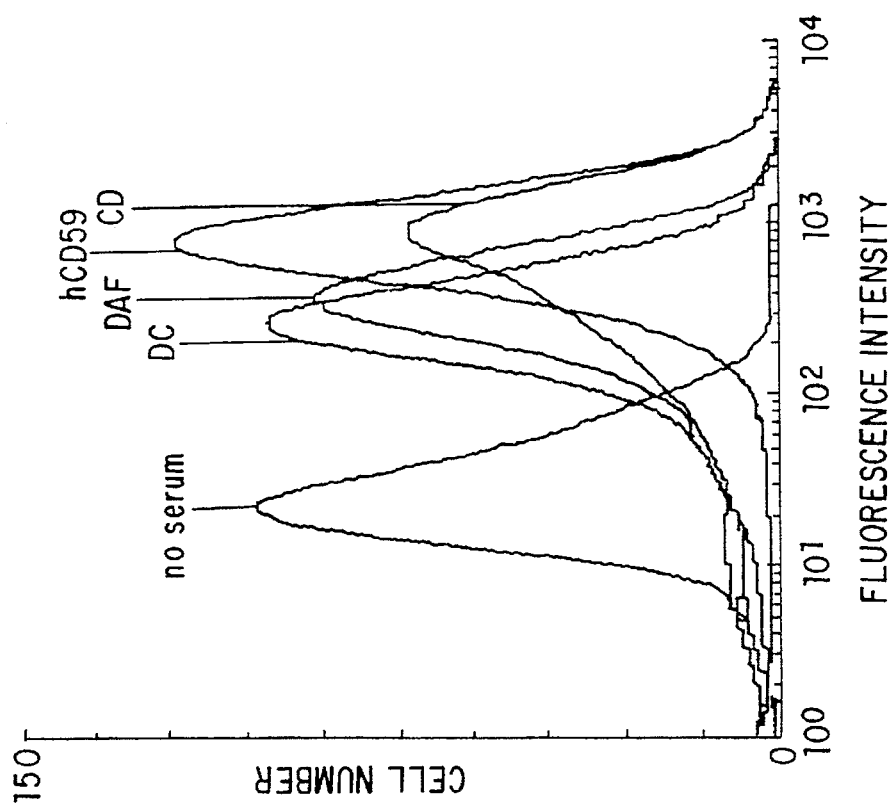
Figure 4C:
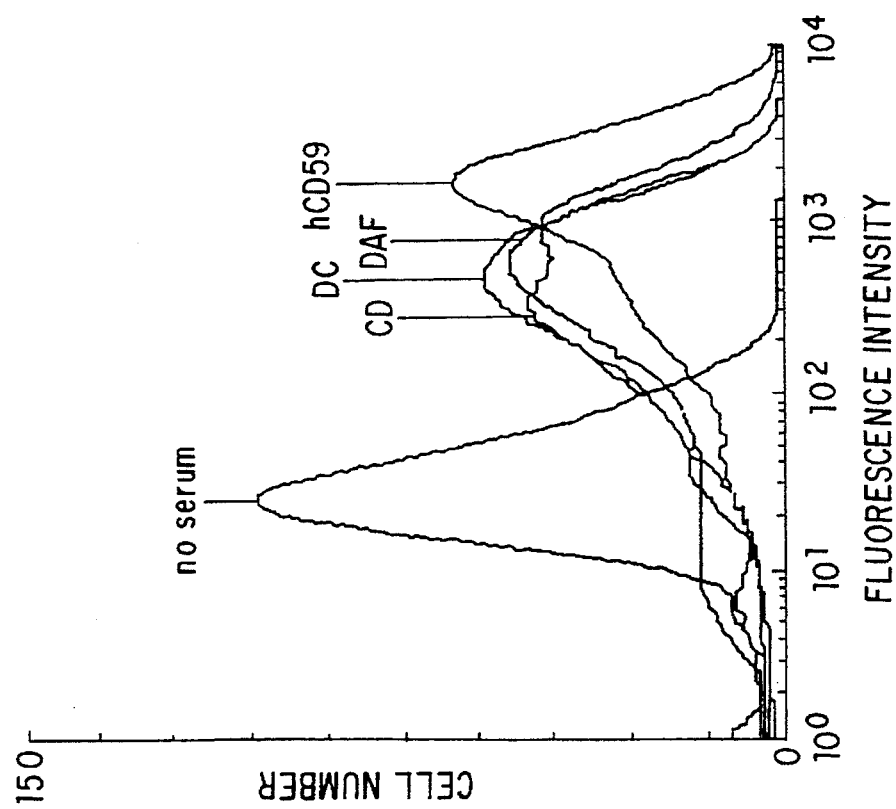

PI-PLC treatment removed the DC protein from the cell surface of the stably transfected Balb/3T3 cell as determined by indirect immunofluorescence using monoclonal antibodies to either CD59 (MEM43; FIG. 3, panel A) or DAF (BRIC216; FIG. 3, panel B). Mock treated cells (–PI-PLC) retained cCIP DC on the cell surface, whereas PI-PLC treatment (+PI-PLC) resulted in the loss of cell surface protein as indicated by reduced fluorescence intensity.

EXAMPLE 5

DC and CD Have C3 Inhibitory Activity Equivalent to That of DAF

The functional activity of DC and CD expressed in transfected Balb/3T3 cells was assessed by measuring their ability to mimic the C3 inhibitory activity of native DAF. This analysis was carried out by incubating the transfected cells with increasing concentrations of human serum (5, 10, 20, and 40%; FIG. 4, panels A–D, respectively) and the cell surface deposition of complement component C3 was assayed by flow cytometry using an anti-C3 monoclonal antibody (anti-C3d, Quidel, San Diego, Calif.).

Transfected Balb/3T3 cells expressing CD59 were prepared as described in copending application Ser. No. 08/205, 720, entitled "Terminal Complement Inhibitor Fusion Genes and Proteins," which is referred to above, the relevant portions of which are incorporated herein by reference. Cells from each of the DAF, CD, DC, and CD59 transfectants were harvested and resuspended in 1×HBSS and 1% BSA. Approximately $1\times10^5$ cells/aliquot were incubated first with an anti-Balb/3T3 complement fixing polyclonal antibody at 4° C. for 30 minutes. The cells were pelleted and washed twice with 1×HBSS and 1% BSA prior to the addition of human serum. The cells were incubated with increasing concentrations of human serum for 30 minutes at 37° C. and were then washed once with 1×HBSS and 1% BSA before being incubated with the anti-C3 monoclonal antibody. The cells were then analyzed by flow cytometry where increasing fluorescence indicates a lack of protection from C3 deposition and therefore a lack of C3 convertase inhibition.

As seen in FIG. 4, DC, CD, and DAF can equally and effectively inhibit the deposition of C3 when challenged with human serum up to 20%. For comparison, cells expressing CD59 alone (also shown in FIG. 4) cannot block the deposition of C3 in that CD59 lacks C3 inhibitory activity.

EXAMPLE 6

Chimeric Complement Inhibitor DC and CD59 Are More Effective Inhibitors of the Lytic Activity of the Membrane Attack Complex than DAF or CD As an additional test of the functional activity of the chimeric complement inhibitor proteins, stably transfected Balb/3T3 cell lines (described in Example 5) expressing DAF, CD59, CD, or DC were assayed for their ability to block the lytic activity of the membrane attack complex (C5b-9).

Figure 5:
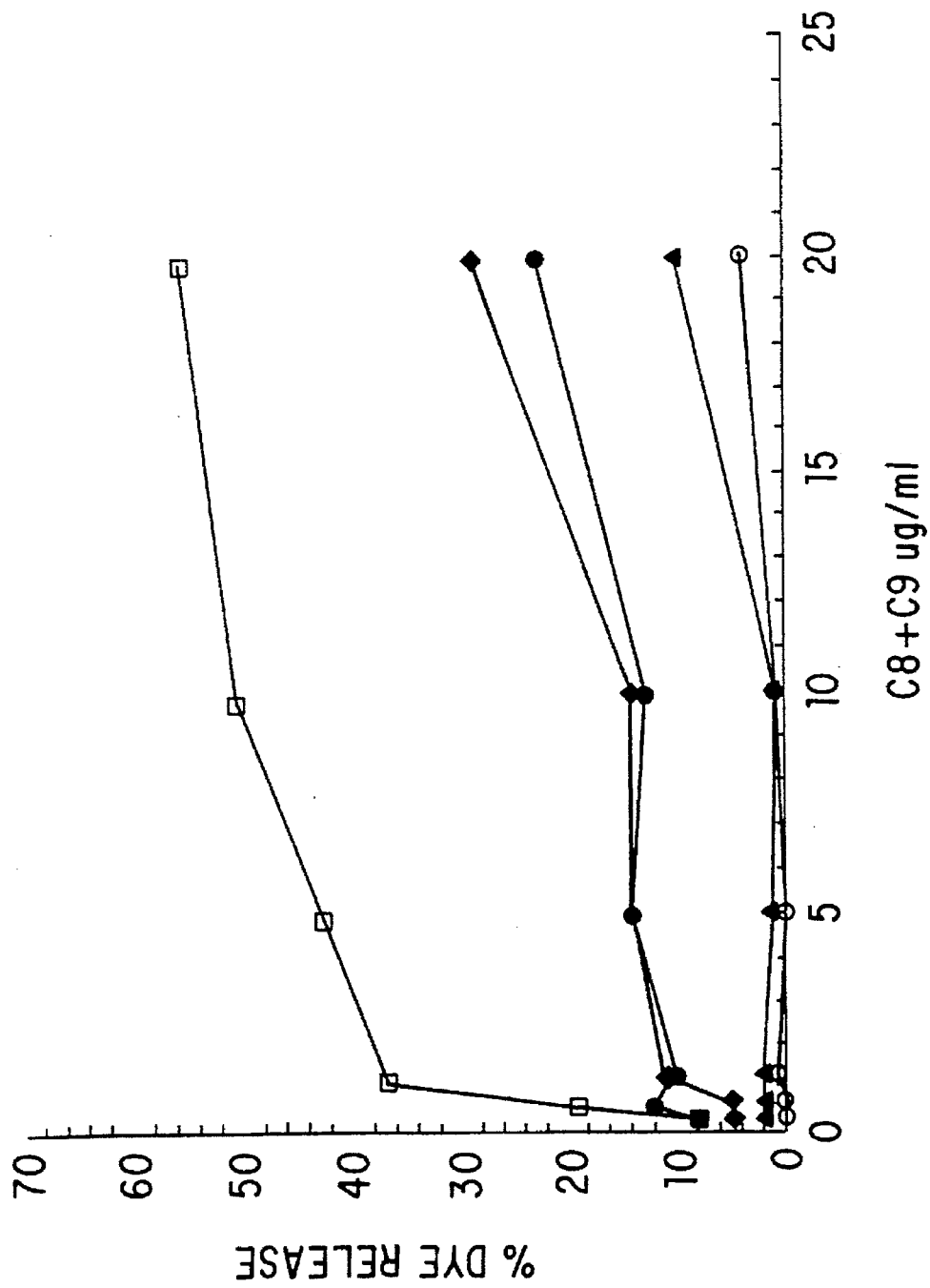
FIG. 5 illustrates the protection of mammalian cells from complement lysis by CD59, DAF, CD, and DC.

The lytic activity of the MAC was assessed by quantitating the efflux of the trapped cytoplasmic indicator dye, Calcein AM (Molecular Probes, Inc., Eugene, Oreg.) from stably transfected Balb/3T3 cells challenged with anti-Balb antibody and human serum (FIG. 5).

Transfected cells expressing DC, CD, DAF, or CD59, as well as vector alone controls, were grown to confluency in 96-well plates. Cells were washed 2×200 μl in HBSS containing 1% (w/v) BSA (HBSS/BSA).

Calcein AM was added (10 μM final) and the plates were incubated at 37° C. for 30 minutes to allow the dye to be internalized by the cells and converted by cellular esterases into a polar fluorescent derivative that is retained inside undamaged cells. The wells were then washed twice with HBSS/BSA to remove dye remaining outside the cells. The cells were then incubated with anti-Balb/3T3 IgG (2 mg/ml in HBSS/BSA), which served as an activator of the classical complement pathway. After a 30 minute incubation at 23° C., unbound IgG was washed away.

The cells were then incubated at 37° C. for 30 minutes in the presence of 25% human C8 deficient serum in HBSS/BSA to allow C5b-7 to assemble on cell surfaces. The cells were then incubated with purified C8 and C9 in HBSS/BSA at the concentrations indicated on the abscissa at 37° C. for 30 minutes to allow the assembly of the MAC and to thus allow complement-mediated damage to occur. (Human C8 depleted serum, as well as purified C8 and C9, were obtained from Quidel Corporation, San Diego, Calif.) The medium bathing the cells was then transferred to a clean 96-well plate for fluorescence measurement.

Under the conditions of this assay, the fluorescent polar derivative of Calcein AM is only released into the medium bathing the test cells if the integrity of the cell membranes is compromised. Therefore, the fluorescence of the Calcein AM released into the medium bathing the test cells versus that retained in the cells provides an indirect, but accurate measure of the level of complement-mediated damage sustained by the cells. Remaining cell-associated dye was determined from a 1% SDS lysate of the cells retained in the 96-well culture plates. This allowed the calculation of percent dye release using the following formulas: Total= released+retained, and, % release=(released÷total)×100. Fluorescence was measured using a Millipore CYTOF-LUOR 2350 fluorescence plate reader (490 nm excitation, 530 nm emission).

The results of the assays, as shown in FIG. 5, demonstrated that DC (closed triangles) and CD59 (open circles) were equally as effective in almost completely blocking the lytic activity of the MAC relative to control cells expressing neomycin resistance alone (open boxes). Complement inhibitors CD (closed circles) and DAF (closed diamonds) were also equally effective although both were less effective at blocking the MAC activity than either CD59 or DC. Comparison of these results with the results of the experiments described in Example 5, which showed that equivalent protection from C3 deposition was provided by CD and DC, but not by CD59, demonstrates that DC, but not CD, provides both C3 convertase and MAC inhibitory activity.

Although preferred and other embodiments of the invention have been described herein, further embodiments may be perceived and practiced by those skilled in the art without departing from the scope of the invention. The following claims are intended to cover the specific embodiments set forth herein as well as such modifications, variations, and equivalents.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

DEPOSITS

Plasmids pC8-hCD59-103, pDC#1-pcDNAI-AMP, and pCDGPI#1-pcDNAI-AMP discussed above, have been deposited with the American Type Culture Collection, 12301 Parklawn Drive, Rockville, Md., 20852, United States of America, in *E. coli*, and have been assigned the designations 69231, 69563, and 69564, respectively. These deposits were made under the Budapest Treaty on the International Recognition of the Deposit of Microorganisms for the Purposes of Patent Procedure (1977).

REFERENCES

Adams, et al., 1991. J. Immunol. 147:3005–3011.
Albrecht, et al., 1992. Virology. 190:527–530.
Ausubel, et al., eds., 1992. "Current Protocols in Molecular Biology", Wiley Interscience, John Wiley and Sons, New York.
Bordet, et al., 1900. Ann. Institut. Pasteur. 14:257.
Bradley. 1987. in Robertson. ed. "Teratocarcinomas and Embryonic Stem Cells a Practical Approach" IRL Press, Eynsham, Oxford, England.
Brasile, et al., 1985. Transplantation. 40:672–675.
Brasile, et al., 1987. Trans. Proceed. 19:894–895.
Brinster, et al., 1985. Proc. Natl. Acad. Sci. USA. 82:4438–4442.
Cosset, et al., 1990. J. Virol. 64:1070–1078.
Chung, et al., 1985. Biochem. 256:133.
Coyne, et al., 1992. J. Immunol. 149:2096.
Dalmasso, et al., 1992. Am. J. Pathol. 140:1157–1166.
Davies, et al., 1989. J. Exp. Med. 170:637–654.
Eglitis, et al., 1988. Biotechniques. 6:608–614.
Fujita et al., 1987. J. Exp. Med. 166:1221.
Gumley, et al., 1992. J. Immunol. 149:2615–2618.
Hogan, et al., 1986. in "Manipulating the Mouse Embryo: A Laboratory Manual". Cold Spring Harbor Laboratory, Cold Spring Harbor, N.Y.
Houle et al., 1988. Blood. 71:280.
Korman, et al., 1987, Proc. Natl. Acad. Sci. USA. 84:2150–2154.
Lovell-Badge. 1987. in Robertson. ed. "Teratocarcinomas and Embryonic Stem Cells a Practical Approach" IRL Press, Eynsham, Oxford, England.
Lublin, et al., 1988. J. Exp. Med. 168:181–194.
Lublin, et al., 1989. Ann. Rev. Immunol. 7:35–58.
Lublin, et al., 1991. J. Exp. Med. 174:35–44.
Luckow, et al., 1988. Bio/Technology. 6:47.
Markowitz, et al., 1988. J. Virol. 62:1120–1124.
McMahon, et al., 1990 Cell. 62:1073–1085.
Medof et al., J. Exp. Med. 160:1558, 1984.
Meri, et al., 1990. Immunology. 71:1–9.
Miller, et al., 1986. Mol. Cell Biol. 6:2895–2902.
Miller, et al., 1989. Biotechniques. 7:981–990.
Moran et al., 1992. J. Immunol. 140:1736–1743.
Morgenstern, et al., 1990. Nucleic Acids Res. 18:3587–3596.
Norris, et al., 1993. Blood. 82:202.
Okada, et al., 1989. J. Immunol. 143:2262–2266.
Pedersen, et al., 1990. Transgenic Techniques in Mice—A Video Guide, Cold Spring Harbor Laboratory, Cold Spring Harbor, N.Y.
Perkins, et al., 1988. Biochemistry. 27:4004.
Petranka, et al., 1992. Proc. Natl. Acad. Sci. USA 89: 7876–7879.
Petranka, et al., 1993. Molec. Immunol. 30:44.
Philbrick, et al., 1990. Eur. J. Immunol. 20:87–92.
Ripoche, et al., 1988. Blochem. J. 249:6122–6126.
Robertson, et al., 1986. Nature. 323:445–448.
Robertson. 1987. in Robertson. ed. "Teratocarcinomas and Embryonic Stem Cells a Practical Approach" IRL Press, Eynsham, Oxford, England.
Roldan, et al., 1990. EMBO J. 9:467–474.
Rollins, et al., 1990. J. Immunol. 144:3478–3483.
Rollins, et al., 1991. J. Immunol. 146:2345–2351.
Rother, et al., 1994. J. Virol. 68:730–737.
Sambrook, et al., 1989. Molecular Cloning: A Laboratory Manual. Second Edition. Cold Spring Harbor Laboratory Press, Cold Spring Harbor, N.Y.
Sandrin, et al., 1993. Proc. Natl. Acad. Sci. USA. 90:11391.
Sawada, et al., 1989. DNA Cell. Biol. 9:213–220.
Shevach, et al., 1989. Immunol. Today. 10:195–200.
Starzl, et al., 1993. Lancet. 341:65–71.
Stefanova, et al., 1989. Mol. Immunol. 26:153–161.
Su, et al., 1991. J. Cell Biol. 112:377–384.
Talib, et al., 1991. Gene. 98:289–293.
Tone, et al., 1992. J. Mol. Biol. 227:971–976.
Venneker, et al., 1992. Exp. Clin. Immunogenet. 9:33–47.
Walsh, et al., 1991. Eur. J. Immunol. 21:847–850.
Whitlow, et al., 1990. Cell. Immunol. 126:176–184.
Williams, et al., 1988. Immunogenetics 27:265–272.
Wing, et al., 1992. Immunology 76:140–145.
Wong, et al., 1985. Proc. Natl. Acad. Sci. USA. 82:7711.
Zhao, et al., 1991. J. Biol. Chem. 266: 13418–13422.

What is claimed is:

1. A chimeric complement inhibitor protein comprising a first functional domain having C3 inhibitory activity and a second functional domain having C5b-9 inhibitory activity; wherein (a) said first functional domain is amino terminal to said second functional domain;

(b) said first functional domain comprises at least a portion of a naturally occurring C3 inhibitor protein;

(c) said second functional domain comprises at least a portion of a naturally occurring C5b-9 inhibitor protein; and (d) the protein has complement inhibitory activity against human complement.

2. The chimeric complement inhibitor protein of claim 1 wherein said chimeric complement inhibitor protein has at least about 25% of the complement inhibitory activity of said naturally occurring C3 inhibitor protein.

3. The chimeric complement inhibitor protein of claim 1 wherein said chimeric complement inhibitor protein has at least about 25% of the complement inhibitory activity of said naturally occurring C5b-9 inhibitor protein.

4. The chimeric complement inhibitor protein of claim 1 wherein the protein includes a linker region between the first and second functional domains.

5. The chimeric complement inhibitor protein of claim 1 wherein the protein includes a transmembrane domain for cell membrane attachment.

* * * * *